(12) United States Patent
Suzuki et al.

(10) Patent No.: US 10,470,942 B2
(45) Date of Patent: Nov. 12, 2019

(54) ABSORBENT ARTICLE AND PRODUCTION METHOD THEREOF

(71) Applicant: DAIO PAPER CORPORATION, Shikokuchuo-shi, Ehime (JP)

(72) Inventors: Migaku Suzuki, Chigasaki (JP); Yoshio Hirai, Tokyo (JP)

(73) Assignee: DAIO PAPER CORPORATION, Shikokuchuo-Shi (JP)

( * ) Notice: Subject to any disclaimer, the term of this patent is extended or adjusted under 35 U.S.C. 154(b) by 455 days.

(21) Appl. No.: 15/023,274

(22) PCT Filed: Sep. 30, 2013

(86) PCT No.: PCT/JP2013/076513
§ 371 (c)(1),
(2) Date: Mar. 18, 2016

(87) PCT Pub. No.: WO2015/045145
PCT Pub. Date: Apr. 2, 2015

(65) Prior Publication Data
US 2016/0235600 A1    Aug. 18, 2016

(51) Int. Cl.
*A61F 13/49* (2006.01)
*A61F 13/494* (2006.01)
(Continued)

(52) U.S. Cl.
CPC .. *A61F 13/49446* (2013.01); *A61F 13/15593* (2013.01); *A61F 13/15804* (2013.01);
(Continued)

(58) Field of Classification Search
CPC ...... A61F 2013/49493; A61F 13/49406; A61F 13/15; A61F 13/49446; A61F 13/49466;
(Continued)

(56) References Cited

U.S. PATENT DOCUMENTS 6,623,466 B1 *  9/2003  Richardson ....... A61F 13/15211
                                                604/385.11
7,264,614 B2 *  9/2007  Minato ............. A61F 13/49019
                                                604/385.01
(Continued)

FOREIGN PATENT DOCUMENTS

JP    H03-231664 A    10/1991
JP    H03234257 A     10/1991
(Continued)

OTHER PUBLICATIONS

Dec. 3, 2013 Written Opinion issued in International Patent Application No. PCT/JP2013/076513.
(Continued)

*Primary Examiner* — Catharine L Anderson
(74) *Attorney, Agent, or Firm* — Oliff PLC

(57) ABSTRACT

An absorber article includes: a body-contact part having a canal member which has a stretchable and shrinkable, left and right pair of head sections extending in the front-rear direction, and which also has a canal sheet having left and right edges joined to the left and right pair of head sections and also having a center section hanging downward, the body contact part also having affixing members which affix the canal member to the wearer's body in such a manner that the head sections of the canal member are in contact with the wearer's skin; and body-non-contacting part having a sheet-like leakage prevention body and also having an absorber disposed on the upper side of the leakage prevention body. The absorber article is also provided with a passage for transporting bodily fluids from the upper side of the canal sheet to the absorber.

16 Claims, 14 Drawing Sheets

Figure 1A:
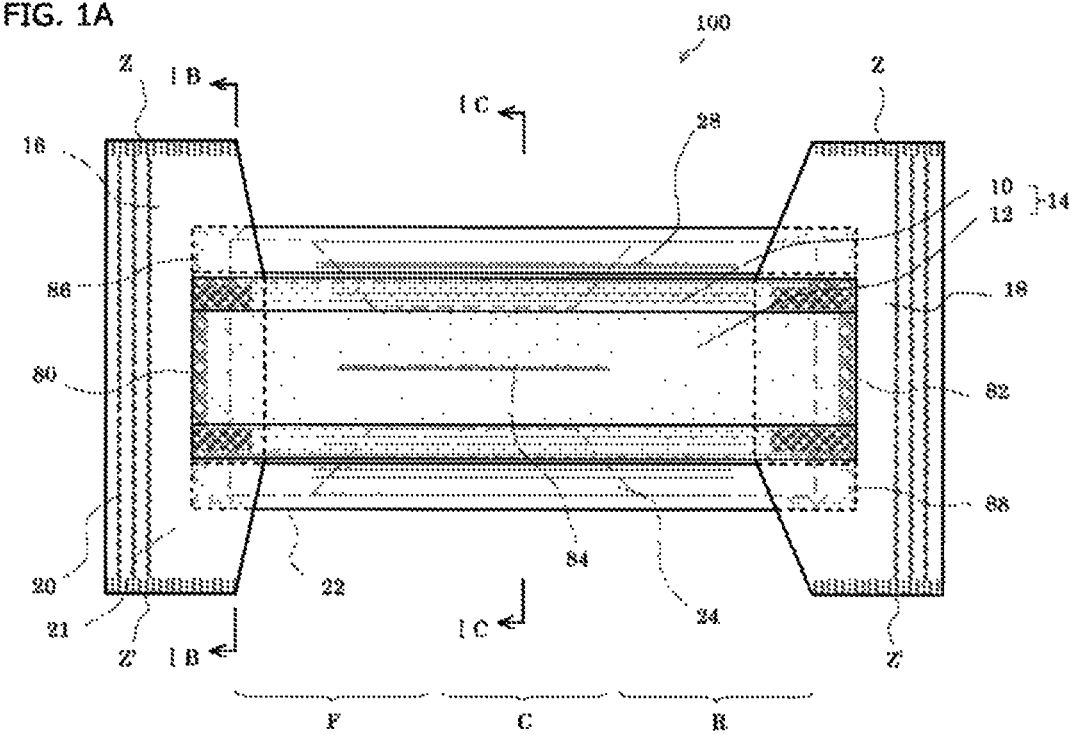

(51) Int. Cl.
*A61F 13/495* (2006.01)
*A61F 13/15* (2006.01)
*A61F 13/496* (2006.01)
*A61F 13/515* (2006.01)
*A61F 13/45* (2006.01)

(52) U.S. Cl.
CPC .......... *A61F 13/495* (2013.01); *A61F 13/496* (2013.01); *A61F 13/4942* (2013.01); *A61F 13/49058* (2013.01); *A61F 13/515* (2013.01); *A61F 2013/4587* (2013.01); *A61F 2013/49042* (2013.01); *A61F 2013/4948* (2013.01); *A61F 2013/4951* (2013.01)

(58) Field of Classification Search
CPC ............ A61F 13/495; A61F 2013/4955; A61F 2013/4956
See application file for complete search history.

(56) References Cited

U.S. PATENT DOCUMENTS

| | | | |
|---|---|---|---|
| 8,062,279 B2 * | 11/2011 | Miyamoto | A61F 13/49017 604/385.04 |
| 9,084,698 B2 * | 7/2015 | Ichikawa | A61F 13/49001 |
| 9,095,478 B2 * | 8/2015 | Roe | A61F 13/15268 |
| 9,308,131 B2 * | 4/2016 | Evenson | A61F 13/49004 |
| 2004/0039363 A1 | 2/2004 | Sugiyama et al. | |
| 2009/0187157 A1 | 7/2009 | Hornung et al. | |
| 2011/0060306 A1 * | 3/2011 | Otsubo | A61F 13/495 604/385.21 |
| 2012/0310193 A1 | 12/2012 | Ostertag | |
| 2015/0080828 A1 | 3/2015 | Suzuki et al. | |
| 2015/0190289 A1 * | 7/2015 | Suzuki | A61F 13/49413 604/385.101 |
| 2015/0196433 A1 | 7/2015 | Suzuki et al. | |

FOREIGN PATENT DOCUMENTS

| | | | |
|---|---|---|---|
| JP | H09-506798 A | | 7/1997 |
| JP | 11244331 A | * | 9/1999 |
| JP | H11-244331 A | | 9/1999 |
| JP | 2000-342623 A | | 12/2000 |
| JP | 2002-143217 A | | 5/2002 |
| JP | 2011-504121 A | | 2/2011 |
| JP | 2011-104001 A | | 6/2011 |
| JP | 5086492 B1 | | 11/2012 |
| JP | 2013-519404 A | | 5/2013 |
| JP | 5236121 B1 | | 7/2013 |
| JP | 5236122 B1 | | 7/2013 |
| WO | 9517147 A1 | | 6/1995 |
| WO | 95/32699 A1 | | 12/1995 |
| WO | 2014/147879 A1 | | 9/2014 |

OTHER PUBLICATIONS

Nov. 26, 2013 Office Action issued in Japanese Patent Application No. 2013-544935.
Mar. 4, 2014 Office Action issued in Japanese Patent Application No. 2013-544935.
Aug. 12, 2014 Office Action issued in Japanese Patent Application No. 2013-544935.
Aug. 25, 2015 Office Action issued in Japanese Patent Application No. 2013-544935.
May 3, 2017 Extended European Search Report issued in Patent Application No. 13894573.8.

* cited by examiner

ABSORBENT ARTICLE AND PRODUCTION METHOD THEREOF

FIELD OF THE INVENTION

The present invention relates to an absorbent article and a production method thereof.

BACKGROUND ART

Absorbent articles are articles, such as diapers (for infants and adults), sanitary napkins, incontinence articles, training pants or the like, that absorb and process bodily fluids excreted from a wearer by means of an absorber that makes use of a super absorbent polymer (hereinafter also referred to as an "SAP"), wood pulp in a fluffy form or the like.

In conventional absorbent articles, a bodily fluid is directly excreted onto the surface of an absorber from the excretory organ of the wearer, and is absorbed into the absorber and processed therein through diffusion over the surface of the absorber and through shifting from the surface of the absorber to the inside thereof.

Accordingly, to prevent bodily fluid from leaking from the absorbent article to the exterior thereof, it is necessary to closely attach the surface of the absorber to the wearer's skin, in particular, the excretory organ, so that no gap is formed between the absorbent article and the wearer's body.

However, when the absorbent article is used in such condition, the wearer's skin becomes closely attached to the surface of the absorber, which is made wet by the bodily fluid, after the bodily fluids are excreted. There existed a problem to the effect that, when the wearer's skin was in contact with the bodily fluid for a prolonged time, it was not only unpleasant for the wearer but also led to swelling of the skin and became a cause of bacterial growth that may lead to rashes and inflammation.

As a new proposal to overcome such problem in conventional absorbent articles, the inventor has proposed an approach in which a unit, which allows shifting and distribution of the bodily fluid to the front and/or rear of the absorber, is newly introduced between the surface of the absorber and the wearer's skin in order to prevent the direct shifting of the bodily fluid to the absorber, in particular, to a crotch part, which is at a position corresponding to the wearer's excretory organ, and thereby, effectively avoiding the contact between the excreted bodily fluid and the wearer's skin.

In Patent Document 1, such unit is proposed as a floating leg gather (FLG). In Patent Document 2, such unit is proposed as a shifting passage for bodily fluids. In Patent Document 3, such unit is proposed as a reception canal for bodily fluids. All of the units according to these proposals share a common point to the effect that they have a pair of right and left head parts and a hanging part that are coupled to the pair of right and left head parts, and that only the pair of right and left head parts make contact with the wearer's skin.

PRIOR ART DOCUMENTS

Patent Documents

[Patent Document 1] JP5086492B1
[Patent Document 2] JP5236121B1
[Patent Document 3] JP5236122B1

SUMMARY OF THE INVENTION

Problems to be Solved by the Invention

In advancing the research on the absorbent articles having the various units described in Patent Documents 1 to 3, the inventor has come to the realization that it may be possible to allow the three-dimensional structure of the unit to be present more stably at the time of wearing and in turn to more effectively avoid the contact between the excreted bodily fluid and the wearer's skin.

Means for Solving the Problems

The inventor has found that, by modularizing the absorbent article into two major components. i.e. a "body-contacting part" without an absorber and a "body-non-contacting part" with an absorber, it is possible to allow the three-dimensional structure of the unit to be present more stably and in turn to more effectively avoid the contact between the excreted bodily fluid and the wearer's skin, and then, completed the present invention.

Namely, the present invention provides the following (1) to (15):

(1) An absorbent article including:
a body-contacting part; and
a body-non-contacting part,
wherein,
the body-contacting part includes
a canal member having a pair of right and left head parts extending in the front-rear direction and having stretchability at at least part thereof, and a canal sheet in which both right and left edges thereof couple to the pair of right and left head parts and in which the center part thereof hangs downward at the time of wearing, and
a fixing member that fixes the canal member to a wearer's body in order to allow the head parts of the canal member to make contact with the wearer's skin at the time of wearing,
the body-non-contacting part includes
a leak preventer in sheet form that prevents leakage of a bodily fluid, and
an absorber arranged on the upper side of the leak preventer and capable of absorbing the bodily fluid,
a passage is provided for transferring the bodily fluid from the upper side of the canal sheet onto a surface of the absorber,
part of an under surface of the canal sheet and part of the surface of the absorber are coupled together,
the absorber is made to maintain a state in which the absorber is spaced apart from the wearer's skin at the time of wearing, and
when the wearer excretes the bodily fluid, the excreted bodily fluid is received on the upper side of the canal sheet, and thereafter the bodily fluid is transferred from the upper side of the canal sheet onto the surface of the absorber through the passage while shifting in the front-and-rear direction.

(2) The absorbent article according to the above-described (1), wherein part of the center part in the lateral direction of the under surface of the canal sheet and part of the surface of the absorber are coupled together at a bottom surface coupling part.

(3) The absorbent article according to the above-described (2), wherein the bottom surface coupling part extends in the front-rear direction in an area including a crotch part.

(4) The absorbent article according to the above-described (2) or (3), wherein part of vicinities of right and left edge parts of the under surface of the canal sheet and part of the surface of the absorber are coupled together at right and left side surface coupling parts.

(5) The absorbent article according to the above-described (4), wherein the right and left side surface coupling parts extend in the front-rear direction in the area including the crotch part.

(6) The absorbent article according to any one of the above-described (1) to (5), wherein the fixing member includes a front covering-part that covers the front body and a rear covering-part that covers the rear body.

(7) The absorbent article according to the above-described (6), including a detachable member that couples the front covering-part and the rear covering-part in a detachable manner.

(8) The absorbent article according to the above-described (6), wherein the front covering-part and the rear covering-part are integrated together and cover around an abdominal part of the wearer at the time of wearing.

(9) The absorbent article according to any one of the above-described (1) to (8), wherein at least part of the canal sheet is liquid impermeable.

(10) The absorbent article according to any one of the above-described (1) to (9), wherein at least part of the fixing member is liquid impermeable.

(11) The absorbent article according to any one of the above-described (1) to (10), wherein right and left edge parts of the leak preventer have stretchable bodies that provide an effect of reducing the length of the right and left edge parts in the front-rear direction.

(12) The absorbent article according to any one of the above-described (1) to (11), wherein the leak preventer assumes a shape which is convex to the lower side at the time of wearing in at least the crotch part.

(13) The absorbent article according to any one of the above-described (1) to (12), wherein the distance between the surface of the absorber and the wearer's skin at the time of wearing becomes 5 mm or more.

(14) The absorbent article according to any one of the above-described (1) to (13), wherein the body-contacting part and the body-non-contacting part are detachable.

(15) A method of producing an absorbent article according to the above described (1) to (14), the method including:
a step of forming each of the body-contacting part and the body-non-contacting part; and
a step of, thereafter, coupling the body-contacting part and the body-non-contacting part.

Effect of the Invention

An absorbent article according to the present invention is capable of effectively avoiding the contact between the excreted bodily fluids and the wearer's skin.

BRIEF DESCRIPTIONS OF THE DRAWINGS

FIG. 1 contains schematic diagrams illustrating an example of an implementation aspect of an absorbent article according to the present invention.

FIG. 2 contains schematic diagrams illustrating an example of an S-part in an absorbent article according to the present invention in the form of a tape-type diaper.

FIG. 3 contains schematic lateral end views illustrating canal members having various canal sheets.

FIG. 4 contains schematic diagrams illustrating canal members having various head parts.

FIG. 5 contains schematic diagrams illustrating various canal members in which the three-dimensional structure of a canal part is easily maintained.

FIG. 6 contains schematic plan views illustrating various S-parts.

FIG. 7 contains schematic diagrams illustrating various R-parts.

FIG. 8 contains schematic diagrams illustrating various R-parts.

FIG. 9 contains schematic lateral end views illustrating various absorbent articles, according to the present invention, at crotch part C.

FIG. 10 contains schematic lateral end views illustrating various absorbent articles, according to the present invention, at crotch part C.

FIG. 11 contains schematic diagrams illustrating another example of an implementation aspect of an absorbent article according to the present invention.

FIG. 12 contains schematic diagrams illustrating a further example of an implementation aspect of an absorbent article according to the present invention.

FIG. 13 contains schematic diagrams illustrating a further example of an implementation aspect of an absorbent article according to the present invention.

FIG. 14 contains schematic diagrams illustrating a further example of an implementation aspect of an absorbent article according to the present invention.

EMBODIMENTS OF THE INVENTION

Hereinafter, absorbent articles according to the present invention will be described in detail, based on the preferred embodiments illustrated in the attached drawings. It should be noted that, in the present specification, when the absorbent article according to the present invention is actually worn, a side close to the skin of the wearer will be referred to as the "top" and a side far therefrom will be referred to as the "bottom/under." In addition, when the absorbent article according to the present invention is actually worn, a side corresponding to the front side of the wearer's body will be referred to as the "front" and a side corresponding to the back side thereof will be referred to as the "rear." Moreover, in order to facilitate understanding, in the respective drawings, members that are actually in contact with each other may be illustrated such that they are spaced apart. In the respective plan views among the attached drawings, the front side of the absorbent article or the like is shown to be positioned at the left side of the corresponding drawing.

In addition, in the present specification, an "absorbent article body" collectively refers to a leak preventer, a top sheet that can be provided above the leak preventer and various other members that can be provided to the absorbent article, all of which are constituent members of the absorbent article. In accordance with this, when the absorbent article is a diaper, the absorbent article body will be referred to as a diaper body.

Moreover, in the present specification, an "absorber surface" refers to a surface of an absorber when it is exposed, or to a surface of a diffusion sheet, acquisition sheet, top sheet (surface sheet), core wrapping sheet or the like when the absorber is covered with such diffusion sheet, acquisition sheet, top sheet (surface sheet), core wrapping sheet or the like.

FIG. 1 contains schematic diagrams illustrating an example of an implementation aspect of an absorbent article according to the present invention. In particular, FIG. 1 shows a pants-type diaper for infants that includes a "body-contacting part (i.e. Skin-contact Part)" (hereinafter also referred to as an "S-part") and a "body-non-contacting part (i.e. Remote Part)" (hereinafter also referred to as an "R-part") and wherein the S-part and the R-part are coupled and integrated with each other at parts thereof.

Figure 1B:
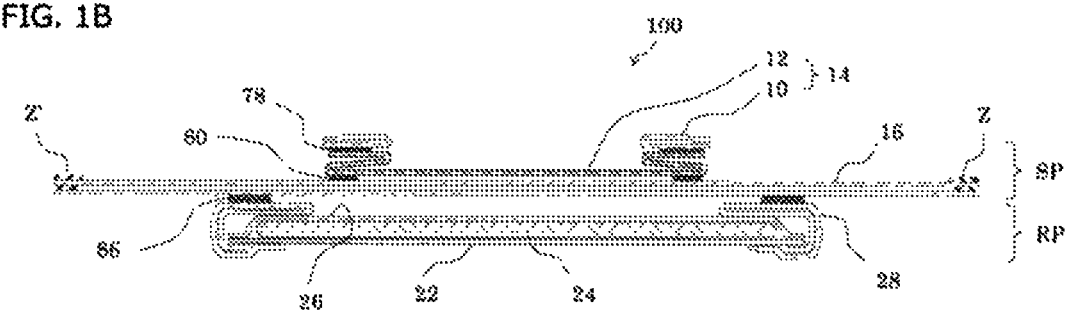
Figure 1C:
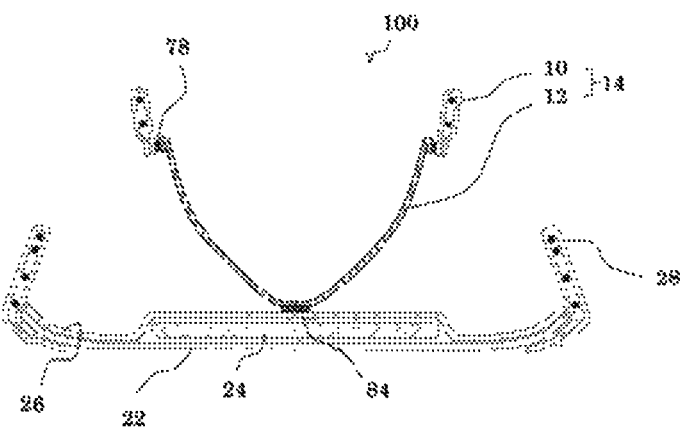

FIG. 1(A) is a developed plan view schematically showing the state (tension state) in which the absorbent article, in the form of a pants-type diaper, is cut at abdominal sealing parts (Z and Z' in FIG. 1(A)) on both the right and left sides of the fixing members of the absorbent article, and in which stress is applied to the absorbent article such that it is pulled in the front-rear direction and the lateral direction in order to be developed into a substantially planar form. FIG. 1(B) is a lateral end view along line IB-IB in FIG. 1(A) in the tension state. FIG. 1(C) is a lateral end view along line IC-IC in FIG. 1(A) when stress is not applied to the absorbent article (relaxed state).

An absorbent article 100 shown in FIG. 1 is configured as a pants-type diaper and is basically provided with an S-part and an R-part. The S-part includes: canal member 14 having a pair of right and left head parts 10 that extend in the front-rear direction and that have stretchability at at least part thereof and canal sheet 12, both the right and left edges thereof being coupled to the pair of right and left head parts 10 and the center part thereof hanging downward at the time of wearing: and a fixing member that fixes canal member 14 to the wearer's body at the time of wearing so that head parts 10 of canal member 14 make contact with the wearer's skin. The R-part includes: leak preventer 22 in sheet form that prevents leakage of bodily fluids; and absorber 24 arranged on the upper side of leak preventer 22 and being capable of absorbing bodily fluids.

The pair of right and left head parts 10 and canal sheet 12 are coupled together at coupling parts 78.

As for the above-described fixing member, front covering-part 16 and rear covering-part 18 that are located around the wearer's waist at the time of wearing are used. Each of front covering-part 16 and rear covering-part 18 includes: in the vicinity of a front end part or a rear end part, waist gather 20 that extends in the lateral direction; and shining gather 21 that also extends in the lateral direction on the side closer to the center part in the front-rear direction than waist gather 20.

In this manner, the fixing member including the front covering-part that covers the front body and the rear covering-part that covers the rear body is one of the preferred embodiments of the present invention.

Front covering-part 16 and rear covering-part 18 are adapted to cover the circumference of the abdominal part of the wearer at the time of wearing, by abdominal sealing parts Z being coupled to each other and abdominal sealing parts Z' being coupled to each other to be integrated into one piece.

In this manner, the front covering-part and the rear covering-part being integrated with each other and covering the circumference of the abdominal part of the wearer at the time of wearing is one of the preferred embodiments of the absorbent article of the present invention. Therefore, the absorbent article according to the present invention can be made into a pants-type diaper.

Both the right and left sides of the under surface of canal sheet 12 are coupled to front covering-part 16 and rear covering-part 18 at the corresponding canal part-front end coupling part 80 and canal part-rear end coupling part 82. This coupling plays a role of hermetically sealing such that leakage of bodily fluids will not occur due to generation of a gap between the front end and right and left edge parts of the canal part.

The entire upper surface of absorber 24 is covered by surface sheet 26.

Belt-like stretchable members 28 extending in the front-rear direction are provided on the right and left edge parts of leak preventer 22. The outer surfaces of stretchable members 28 are coupled to front covering-part 16 and rear covering-part 18 at the corresponding R-part-front end coupling part 86 and R-part-rear end coupling part 88. The purpose of this coupling is to integrate the R-part and the S-part together, and it is sufficient when the coupling is made such that the R-part and the S-part do not disengage from each other, and airtightness is not necessary. Stretchable members 28 provide an effect of preventing the side edge parts of absorber 24 from hanging downward. Stretchable members 28 need not to be in direct contact with the wearer's skin.

Absorbent article 100 is in an aspect where an R-part includes stretchable members 28; however, in the present invention, it may also not include a stretchable member.

In absorbent article 100, micro-openings are provided in a non-woven fabric that constitutes canal sheet 12, as a passage for transferring bodily fluids from the upper side of canal sheet 12 onto the surface of absorber 24.

Part of an under surface of canal sheet 12 (i.e. the underside surface of the bottom surface of the canal part configured by canal sheet 12) and part of the surface of absorber 24 (i.e. the surface of surface sheet 26) are coupled together at linear bottom surface coupling part 84.

The peripheries of the front end part and the rear end part of the R-part are respectively coupled, in a belt-like form and in part, to front covering-part 16 and rear covering-part 18 of the S-part.

In this manner, the S-part and the R-part are prevented from being disengaged.

As shown in FIG. 1(C), the canal part of the S-part assumes a V-shape or U-shape in the relaxed state, and only the pair of right and left head parts 10 having stretchability at at least part thereof make contact with the wearer's skin.

The R-part including absorber 24 is ensured to be spaced apart from the wearer's skin. This is due to the fact that, by modularizing each of the S-part and the R-part, the bottom surface part of the canal part is pulled downward and the settling or deformation of the entire canal part is reduced due to the weight of the absorber contained in the R-part, and in particular, that the three-dimensional structure in V-shape or U-shape is easily maintained at crotch part C and thus, the three-dimensional structure of the unit is present thereat in a stable manner.

Specifically, it is preferred that the distance between the surface of the absorber (or the surface sheet or the like covering the absorber) and the wearer's skin is 5 mm or more at the time of wearing.

In the absorbent articles described in Patent Documents 1 to 3, the absorber and the FLGs or the like are integrated together and a physical constraint mainly due to the absorber with respect to the portions of the FLGs, etc. is present. This obstructs the stabilization of the three-dimensional structure. However, in the absorbent articles according to the present invention, for example, in absorbent article 100, the coupling is only made, at the crotch part, with the surface of absorber 24 by means of bottom surface coupling part 84. Accordingly, the three-dimensional structure of the canal part in the S-part is less susceptible to the influence of the R-part, and thus, it can be present thereat in a stable manner.

For this reason, a gap is now present between the side surfaces of canal sheet 12 and surface sheet 26 covering absorber 24.

In absorbent article 100, a bodily fluid excreted from the wearer is excreted to the inner side of the canal part from the opening between the pair of right and left head parts 10 and is received on the upper side of canal sheet 12. Thereafter, it shifts within the canal part in the front-rear direction and is transferred from the upper side of canal sheet 12 onto the surface of absorber 24 through a passage configured by the micro-openings.

The receipt and shifting of the bodily fluid are carried out extremely smoothly, since the canal part is present in a stable manner.

According to the present invention, by making the S-part and the R-part a separate body, the configuration, size, and shape or the like of the absorber can be designed relatively freely. Thus, diversification of products becomes easy.

In conventional absorbent articles, the length and width of the absorber are required to be designed within the ranges of length in the front-rear direction and width in the lateral direction of the absorbent article, and in particular, to be designed so as to adapt to the narrowed portion of the crotch part of the wearer.

In the present invention, since the R-part including the absorber is at a position spaced apart from the wearer's skin, the adaptation with respect to the narrow portion of the crotch part is not necessary. For example, it is possible to have a short length corresponding to the crotch part, while the width in the lateral direction can be made wide.

In addition, in the present invention, by configuring the absorbent article by means of two modules, i.e. an S-part and an R-part, the structure itself is simplified, the number or types of members may be reduced, the weight may be decreased, and further, the production cost becomes cheaper.

Hereinafter, the S-part and the R-part will be described in detail.

1. General Structure and State of Existence of S-Part

Figure 2A:
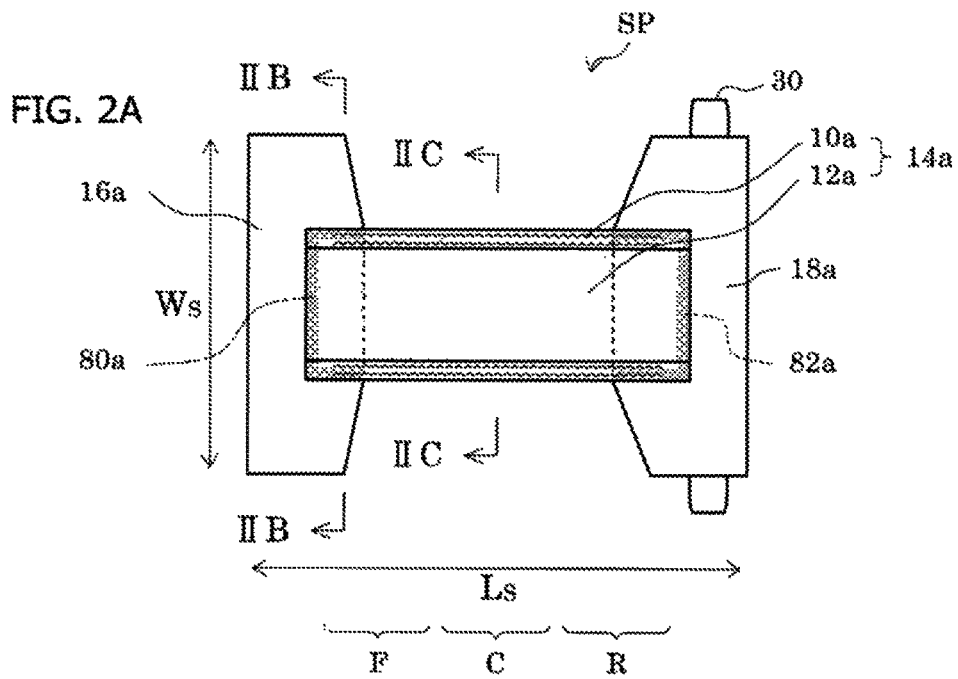
Figure 2B:
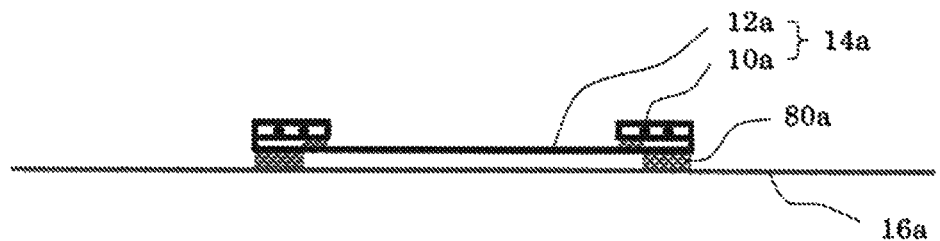
Figure 2C:
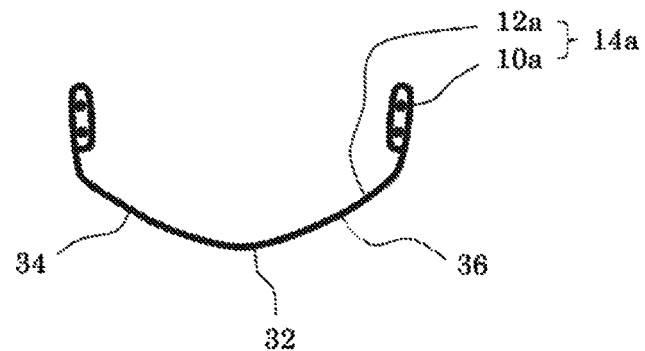

FIG. 2 contains schematic diagrams illustrating an example of an S-part in an absorbent article according to the present invention in the form of a tape-type diaper. FIG. 2(A) is a developed plan view schematically showing the state (tension state) in which stress is applied to the S-part such that it is pulled in the front-rear direction and the lateral direction in order to be developed into a substantially planar form. FIG. 2(B) is a lateral end view along line IIB-IIB in FIG. 2(A) in the tension state. FIG. 2(C) is a lateral end view along line IIC-IIC in FIG. 2(A) when stress is not applied to the S-part (relaxed state).

S-part SP shown in FIG. 2 extends in the front-rear direction, and includes: canal member 14a; and front covering-part 16a and rear covering-part 18a. Canal member 14a has a pair of right and left head parts 10a having stretchability at at least part thereof and canal sheet 12a, in which both edges thereof couple to the pair of right and left head parts 10a and a center part thereof hangs downward at the time of wearing. Front covering-part 16a and rear covering-part 18a are located around the abdominal part of the wearer at the time of wearing and function as a fixing member that fixes canal member 14a to the wearer's body such that head parts 10a of canal member 14a make contact with the wearer's skin.

The length in the front-rear direction of the S-part is equal to the length (total length) $L_s$ in the front-rear direction of the absorbent article. The width in the lateral direction of the S-part is equal to the width (total width) $W_s$ in the lateral direction of the absorbent article. Both length and width can be set, as needed, depending on the size of the absorbent article (for example, S size (for body weight of approximately 4 to 8 kg), M size (for body weight of approximately 6 to 11 kg), L size (for body weight of approximately 9 to 14 kg), Big size (for body weight of approximately 12 to 20 kg) and Super Big size (for body weight of approximately 13 to 25 kg)).

Detachable members 30 are provided on both the right and left sides of rear covering-part 18a. Detachable members (not shown) are also provided on the under surface of front covering-part 16a, such that they can be detached from detachable members 30. These detachable members may be configured by, for example, various hook-and-loop fasteners. In particular, as for detachable members 30 provided on both the right and left sides of rear covering-part 18a, adhesive tape or Velcro tape (male) may be used. As for the detachable members provided on the under surface of leak preventer 22 of front covering-part 16a, tape landing zones (TLZs) (female) or zipper landing zones (ZLZs) (female) may be used.

In this manner, having detachable members for making the front covering-part and the rear coveting-part couple with each other in a detachable manner is one of the preferred embodiments of the present invention. Therefore, the absorbent article according to the present invention can be made into a tape-type diaper.

As shown in the lateral end view of the front covering-part in FIG. 2(B), both the right and left sides of the under surface of canal sheet 12a are coupled to front covering-part 16a at canal part-front end coupling parts 80a. This coupling plays a role of hermetically sealing such that leakage of bodily fluids will not occur due to generation of a gap between the front end and right and left edge parts of the canal part. In particular, the coupling is made without any space therebetween by means of an adhesive such as a hot-melt adhesive or the like.

At the time of wearing, as shown in FIG. 2(C), canal sheet 12a hangs down from the pair of right and left head parts 10.

The canal part is formed by canal bottom surface 32, which is configured by the vicinity of the center part in the lateral direction of canal sheet 12a, canal left side surface part 34, which is configured by the part of canal sheet 12a hanging down from the left side head part 10a, and canal right side surface part 36, which is configured by the part of canal sheet 12a hanging down from the right head part 10a.

The canal part can be sectionalized, in the front-rear direction, into three regions of front body F, crotch part C and rear body R.

The depth of the canal part is largest at crotch part C and the canal part takes on a three-dimensional structure having a V-shaped or U-shaped cross section.

2. Configuration of Canal Member (1) Canal Sheet

FIG. 3 contains schematic lateral end views illustrating canal members having various canal sheets.

Figure 3A:
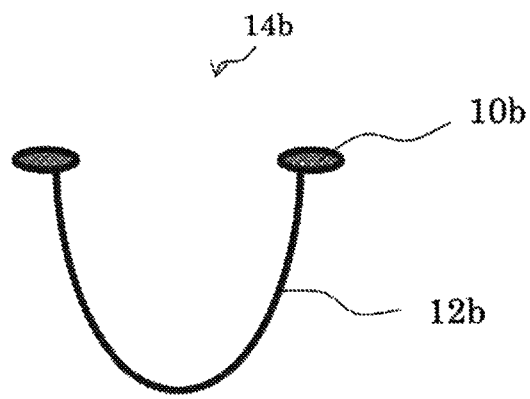

Canal member 14b shown in FIG. 3(A) has the right and left edge parts of canal sheet 12b being coupled to the pair of right and left head parts 10b and has the vicinity of the center part of canal sheet 12b hanging down such that a V-shaped or U-shaped cross section is obtained. The right and left edge parts of canal sheet 12b may cover the pair of right and left head parts 10b.

Figure 3B:
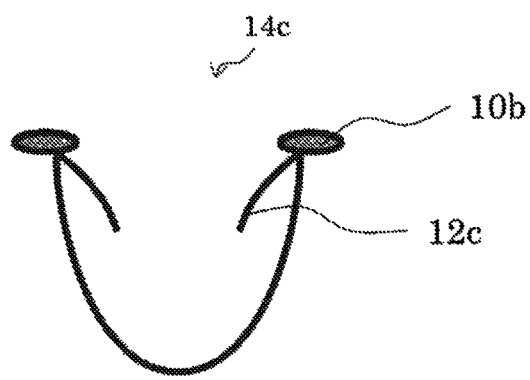

Canal member 14c, shown in FIG. 3(B), is similar to canal member 14b shown in FIG. 3(A) with respect to the point that it has the right and left edge parts of canal sheet 12c being coupled to the pair of right and left head parts 10b and has the vicinity of the center part of canal sheet 12c hanging down such that a V-shaped or U-shaped cross section is obtained. However, the right and left end parts of canal sheet 12c further extend to the inner side from the coupling parts with head parts 10b and hang down therefrom.

These extension parts are usually designed relatively short, as shown in FIG. 3(B). The extension parts serve as guide sheets when receiving a bodily fluid in the canal part and also provide a function of preventing the temporarily received and staying bodily fluid from overflowing to the outside of the canal part.

The right and left edge parts of canal sheet 12c may cover the pair of right and left head parts 10b.

Figure 3C:
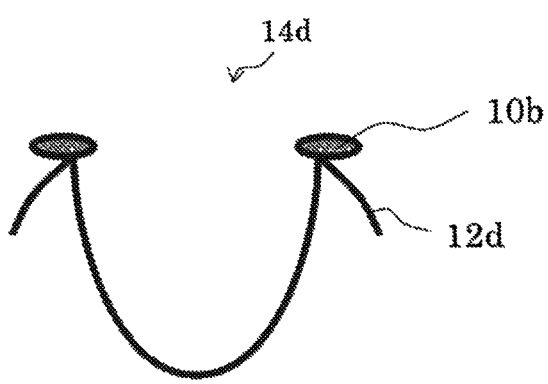

Canal member 14d, shown in FIG. 3(C), is similar to canal member 14b shown in FIG. 3(A) with respect to the point that it has the right and left edge parts of canal sheet 12d being coupled to the pair of right and left head parts 10b and has the vicinity of the center part of canal sheet 12d hanging down such that a V-shaped or U-shaped cross section is obtained. However, the right and left end parts of canal sheet 12d further extend to the outer side from the coupling parts with head parts 10b and hang down therefrom.

These extension parts can be designed relatively short, as shown in FIG. 3(C). These relatively-short extension parts provide a function of fluid guidance for collecting the bodily fluid onto the absorber (not shown) when the amount of bodily fluid exceeds head parts 10b.

When the extension parts are designed relatively long, and for example, the absorber (not shown) is coupled to and arranged on canal member 14d, the extension parts serve as parts covering the side surfaces of the absorber or parts coupled to the right and left edge parts of the absorber.

The right and left edge parts of canal sheet 12d may cover the pair of right and left head parts 10b.

As for the material for the canal sheet, a non-woven fabric may be used. A non-woven fabric preferably has a relatively low basis weight. In particular, a basis weight of 10 to 30 $g/m^2$ is preferred.

As for the non-woven fabric, for example, a non-woven fabric that uses synthetic fiber as a raw material (for example, a spun-melt non-woven fabric such as a spunbonded (SB) non-woven fabric, a spunbonded-meltblown laminated body (SMS, SMMS) or the like, having PE, PP, PET or a composite fiber thereof as a raw material, a spot-bonded non-woven fabric having a carded web coupled thereto, a hydroentangled (also referred to as spunlaced) non-woven fabric and an air-through non-woven fabric) may be used independently or in combination.

The above-described non-woven fabric that uses synthetic fiber as a raw material is usually hydrophobic and thus, it is also possible to use a non-woven fabric being entirely or partially applied with hydrophilic processing by way of treating the fabric with a surfactant in order to provide permeability of the bodily fluid thereto.

According to the present invention, a liquid impermeable non-woven fabric, which is hydrophilic on the inner surface sides of the canal part, which are configured by the upper surface of the canal sheet and which is hydrophobic on the outer surface sides of the canal part, which are configured by the under surface of the canal sheet, is preferably used as the canal sheet.

When this non-woven fabric is used as the canal sheet, the receipt and shifting of bodily fluids on the inner surface sides of the canal part are carried out smoothly. In this manner, the leakage of bodily fluids to the outside of the canal part from parts other than the exit for bodily fluids is effectively prevented.

In particular, a laminated body may be provided in which a hydrophilic non-woven fabric (for example, a rayon non-woven fabric and a cotton non-woven fabric) or tissue paper is partially laminated onto, for example, a hydrophobic non-woven fabric (for example, a PP SMS non-woven fabric). Such laminated body is arranged such that surfaces of the hydrophilic non-woven fabric or tissue paper constitute the inner surfaces of the canal part, and such that surfaces of the hydrophobic non-woven fabric constitute the outer surfaces of the canal part.

In addition, a laminated body may be provided in which a hydrophobic film (for example, a PE film) is laminated onto, for example, a non-woven fabric applied with hydrophilic treatment. Such laminated body is arranged such that surfaces of the non-woven fabric applied with the hydrophilic treatment constitute the inner surfaces of the canal part, and such that surfaces of the hydrophobic film constitute the outer surfaces of the canal part.

According to the present invention, at least part of the canal sheet is preferably liquid impermeable. In this case, the receipt and shifting of bodily fluids are carried out more smoothly.

(2) Head Part

FIG. 4 contains schematic diagrams illustrating canal members having various head parts. FIG. 4(A), FIG. 4(C), FIG. 4(E), FIG. 4(G) and FIG. 4(I) are respectively lateral end views in the relaxed state. FIG. 4(B), FIG. 4(D), FIG. 4(F), FIG. 4(H) and FIG. 4(J) are respectively plan views in the tension state.

Figure 4A:
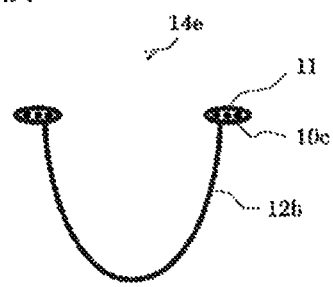
Figure 4B:
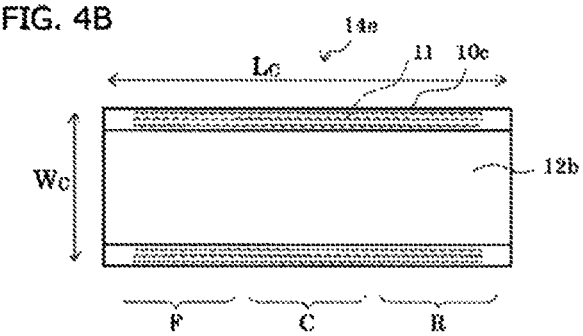

Canal member 14e shown in FIG. 4(A) and FIG. 4(B) includes: canal sheet 12b (for example, a PE/PP spunbonded non-woven fabric having, for example, a basis weight of 15 $g/m^2$); and a pair of right and left head parts 10c, which are formed by arranging, at the right and left edge parts of canal sheet 12b, three pieces of filament-like elastic yarn 11 (such as polyurethane filaments having, for example, 600 dtex) in a parallel manner and covering the same.

As shown in FIG. 4(B), elastic yarn 11 is arranged over the entire length, except for the vicinities of both the front and rear end parts, from front body F to rear body R via crotch part C.

Elastic yarn 11 of head part 10c is covered by canal sheet 12b and is adhered thereonto in a state in which stress is applied thereto in the front-rear direction such that it is stretched. After adhesion, when elastic yarn 11 is put into the relaxed state by releasing the stress, elastic yarn 11 contracts and becomes short. Accordingly, head part 10c has stretchability by the right and left edge parts of canal sheet 12b and elastic yarn 11 being integrated together.

In canal member 14e, the right and left edge parts of canal sheet 12b are coupled to the pair of right and left head parts 10c and the center part of canal sheet 12b hangs downward such that a V-shaped or ti-shaped cross section is obtained.

Figure 4C:
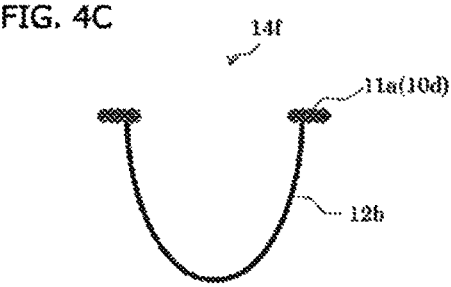
Figure 4D:
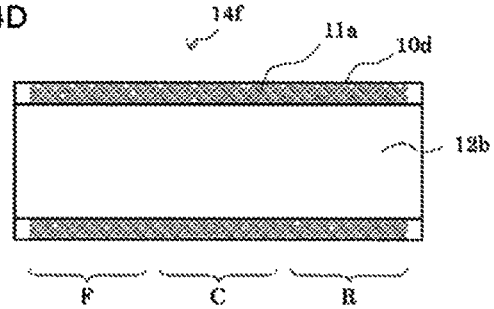

Canal member 14f shown in FIG. 4(C) and FIG. 4(D) includes: canal sheet 12b (such as a PE/PP spunbonded non-woven fabric having, for example, a basis weight of 15 g/m); and a pair of right and left head parts 10d made of bulky foam member 11a (such as a soft foam sheet made of polyurethane (for example, polyether-based polyurethane) having, for example a width of 15 mm and a thickness of 4 mm), wherein the right and left edge parts of canal sheet 12b are coupled to the under surface of head parts 10d.

As shown in FIG. 4(D), foam member 11a is arranged over the entire length, except for the vicinities of both the front and rear end parts, from front body F to rear body R via crotch part C.

Foam member 11a of head part 10d is covered by canal sheet 12b and is adhered thereonto in a state in which stress is applied thereto in the front-rear direction such that it is stretched. After adhesion, when foam member 11a is put into the relaxed state by releasing the stress, foam member 11a contracts and becomes short. Accordingly, head part 10d has stretchability.

In canal member 14f, the right and left edge parts of canal sheet 12b are coupled to the pair of right and left head parts 10d and the center part of canal sheet 12b hangs downward such that a V-shaped or U-shaped cross section is obtained.

Figure 4E:
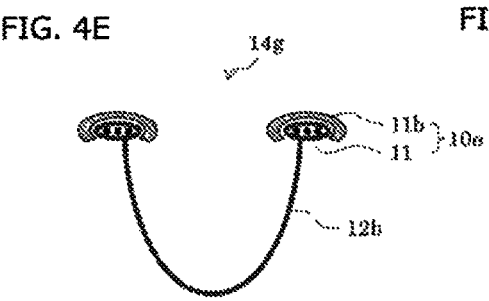
Figure 4F:
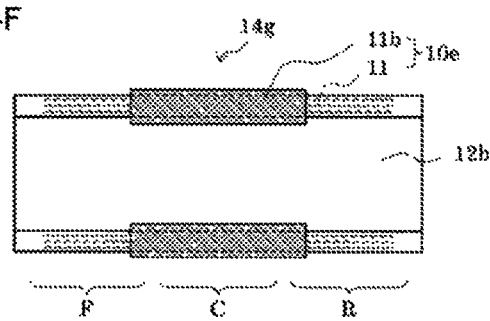

Canal member 14g shown in FIG. 4(E) and FIG. 4(F) is a combination of canal member 14e shown in FIG. 4(A) and FIG. 4(B) and foam member 11b (such as a soft foam sheet made of polyurethane (for example, polyether-based polyurethane) having, for example, a width of 25 mm and a thickness of 3 mm). More specifically, head part 10e is made up of a combination of two types of elastic member, i.e. elastic yarn 11 and foam member 11b.

As shown in FIG. 4(F), elastic yarn 11 is arranged over the entire length, except for the vicinities of both the front and rear end parts, from front body F to rear body R via crotch part C. On the other hand, foam member 11b is arranged at a position that includes crotch part C and parts of front body F and rear body R. The foam member may also be arranged over the entire length, as with the elastic yarn; however, arranging the same only on parts as shown in FIG. 4(F) is cheaper.

Figure 4G:
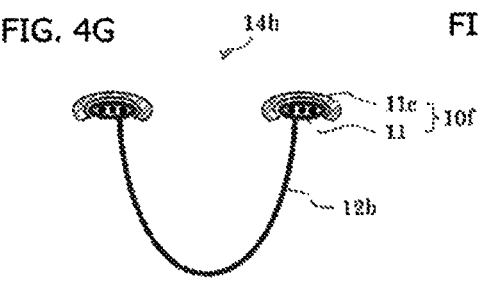
Figure 4H:
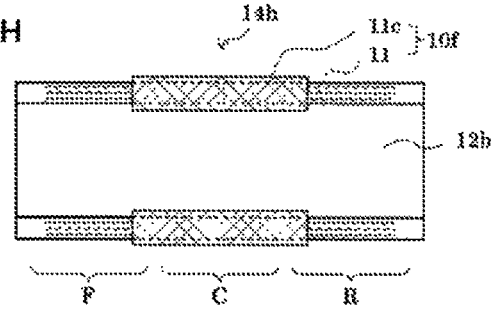

Head part 10e can be made extremely bulky (for example, having a thickness of 7 to 8 mm) at crotch part C in the relaxed state, by means of three pieces of elastic yarn 11 and foam member 11b that covers the side surfaces of the elastic yarn and the upper part thereof. In this manner, head part 10e can be made bulky and it has a cushioning property, and good adhesion can be obtained between head part 10e and the wearer's skin at the crotch part Canal member 14h, shown in FIG. 4(G) and FIG. 4(H), is similar to canal member 14g shown in FIG. 4(E) and FIG. 4(F); however, it differs therefrom with respect to the point that, instead of foam member 11b, rubber sheet member 11c (such as a silicone rubber sheet having, for example, a width of 20 mm and a thickness of 2 mm) is used. More specifically, head part 10f is made up of a combination of two types of elastic member, i.e. elastic yarn 11 and rubber sheet 11c.

The function of canal member 14h is similar to that of canal member 14g.

Figure 4I:
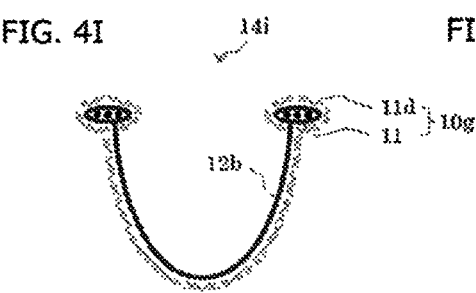
Figure 4J:
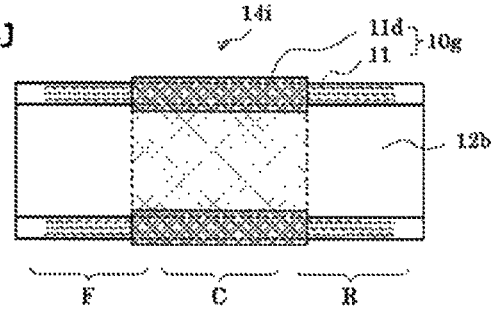

Canal member 14i, shown in FIG. 4(I) and FIG. 4(J), is similar to canal member 14g shown in FIG. 4(E) and FIG. 4(F); however, it differs therefrom with respect to the point that, instead of foam member 11b, foam member 11d (such as a polyethylene foam sheet having, for example, a width of 180 mm and a thickness of 3 mm) is used. More specifically, foam member 11d constitutes head part 10g by covering elastic yarn 11 and it further covers canal sheet 12b from the underside (the outer side). Foam member 11d and canal sheet 12b are adhered and integrated together by means of an adhesive or the like.

As shown in FIG. 4(J), elastic yarn 11 is arranged over the entire length, except for the vicinities of both the front and rear end parts, from front body F to rear body R via crotch part C. On the other hand, foam member 11d is arranged at a position that includes crotch part C and parts of front body F and rear body R. The foam member may be arranged over the entire length, as with the elastic yarn; however, arranging the same only on parts as shown in FIG. 4(J) is cheaper.

Head part 10g is made up of a combination of two types of elastic member, i.e. elastic yarn 11 and foam member 11d.

In this manner, head part 10g can be made bulky and it has a cushioning property, and good adhesion can be obtained between head part 10g and the wearer's skin at the crotch part.

In addition, canal sheet 12b is covered by foam member 11d at crotch part C. Thus, the stiffness of canal member 14i becomes higher at crotch part C, the settling or deformation of canal member 14i due to the application of weight that occurs due to a change in body position, etc. of the wearer at the time of wearing is reduced, and it becomes easy to maintain, all the time, the V-shaped or U-shaped three-dimensional structure shown in FIG. 4(I), and, in turn, the receipt and shifting of bodily fluids can be carried out in a stable manner.

In addition, if a liquid impermeable material (for example, the above-described polypropylene foam sheet) is used for foam member 11d, even when a hydrophilic non-woven fabric is used for canal sheet 12b, the shifting of bodily fluids from the canal part at crotch part C to the outside thereof can be prevented.

As described above, in canal member 14i, the degree of freedom in product design can be increased by means of combining different functional materials.

In any of the canal members, length $L_c$ (total length) in the front-rear direction of the canal member is shorter than total length $L_s$ of the absorbent article and width $W_c$ (total width) in the lateral direction of the canal member is shorter than total length $W_s$ of the absorbent article (see FIG. 4(B)).

(3) Three-Dimensional Structure of Canal Member

In order for the canal part, which relates to the receipt and shifting of bodily fluids, to fulfill its function in a stable manner, it is necessary for the three-dimensional structure having a V-shaped or U-shaped cross section to be maintained at the time of wearing.

To this end, it is preferable to prevent the canal part from being jammed and being deformed in a major way, which is caused by the application of weight or the difference in gap status due to the movement of the body or the body position change of the wearer at the time of wearing. In particular, at crotch part C and the regions around such crotch part C where the depth of the canal part becomes large, it is preferable to firmly maintain the three-dimensional structure.

FIG. 5 contains schematic diagrams illustrating various canal members in which the three-dimensional structure of a canal part is easily maintained. FIG. 5(A), FIG. 5(C), FIG. 5(E), FIG. 5(G) and FIG. 5(I) are respectively lateral end views in the relaxed stated. FIG. 5(B), FIG. 5(D), FIG. 5(F), FIG. 5(H) and FIG. 5(J) are respectively plan views in the tension state.

Figure 5A:
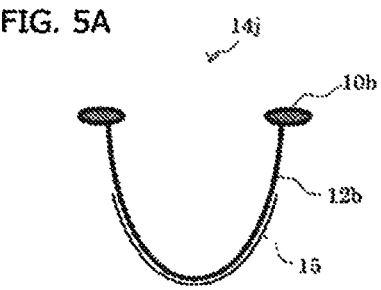
Figure 5B:
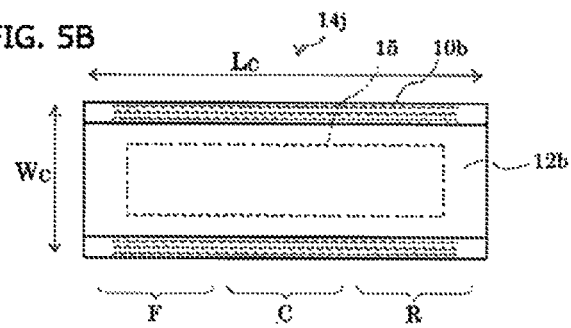

Canal member 14j, shown in FIG. 5(A) and FIG. 5(B), is similar to canal member 14b shown in FIG. 3(A); however, liquid impermeable film 15 (such as PE film (for example, an air permeable film that allows CaCO3 to coexist in LDPE resin) having, for example, a thickness of 20 μm) is provided on the underside (the outer side) of canal sheet 12b (such as a hydrophilic non-woven fabric (for example, a PET air-through non-woven fabric)).

Liquid impermeable film 15 is provided over substantially the entire length of canal member 14j in the front-rear direction and is provided so as to cover the bottom surface part and parts of left side surface part and right side surface part of the canal part in the lateral direction. Canal sheet 12b and liquid impermeable film 15 are adhered to each other by means of an adhesive such as a hot-melt adhesive or the like.

In canal member 14j, since canal sheet 12b is covered by liquid impermeable film 15, the bottom surface and parts of the left side surface part and right side surface part of the canal part obtain liquid impermeability (leak prevention property), canal sheet 12b is reinforced, the settling phenomenon of the canal part is alleviated, deformation is reduced, and thus, the V-shaped or U-shaped three-dimensional structure can be easily maintained over substantially the entire length.

Figure 5C:
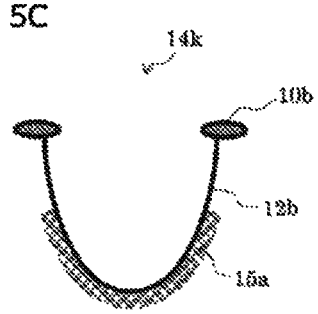
Figure 5D:
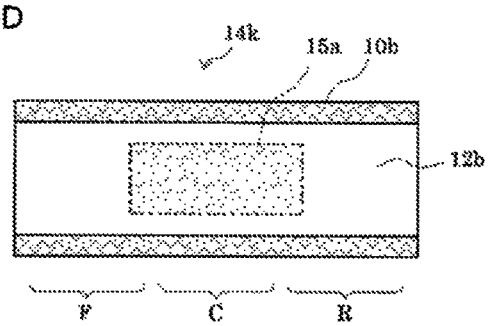

Canal member 14k, shown in FIG. 5(C) and FIG. 5(D), is similar to canal member 14b shown in FIG. 3(A); however, liquid impermeable foam member 15a (such as a soft foam sheet made of polyurethane (for example, polyether-based polyurethane) having, for example, a thickness of 2 mm) is provided on the underside (the outer side) of canal sheet 12b (such as a hydrophilic non-woven fabric (for example, a PET air-through non-woven fabric)).

Liquid impermeable foam member 15a is provided over crotch part C and the periphery thereof of canal member 14k in the front-rear direction and is provided so as to cover the bottom surface part and parts of left side surface part and right side surface part of the canal part in the lateral direction. Canal sheet 12b and liquid impermeable foam member 15a are adhered to each other by means of an adhesive such as a hot-melt adhesive or the like.

In canal member 14k, since canal sheet 12b is covered by liquid impermeable foam member 15a, the bottom surface part and parts of the left side surface part and right side surface part of the canal part obtain liquid impermeability (leak prevention property), canal sheet 12b is reinforced, the settling phenomenon of the canal part is alleviated, deformation is reduced, and thus, the V-shaped or U-shaped three-dimensional structure can be easily maintained over the area centered around crotch part C, and also, deformation is reduced in the area around crotch part C.

Figure 5E:
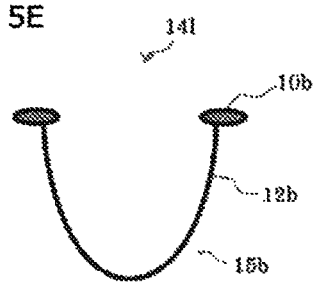
Figure 5F:
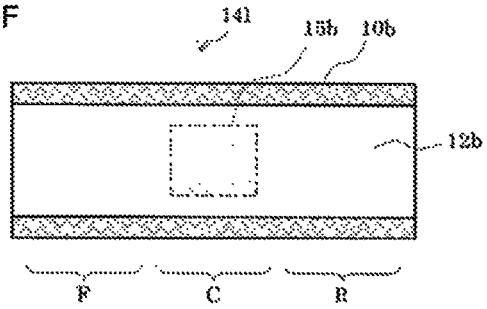

Canal member 14l, shown in FIG. 5(E) and FIG. 5(F), is similar to canal member 14b shown in FIG. 3(A); however, liquid impermeable foam member 15b (such as foam polystyrene (for example, those used for insulating containers used for shipping frozen food), rigid urethane foam having, for example, a thinnest part of 5 mm and a thickest part of 15 mm) is provided on the underside (the outer side) of canal sheet 12b (such as a hydrophilic non-woven fabric (for example, a PET air-through non-woven fabric)).

Liquid impermeable foam member 15b is provided to crotch part C of canal member 14l in the front-rear direction and is provided so as to cover the bottom surface part and parts of the left side surface part and the right side surface part of the canal part in the lateral direction. Canal sheet 12b and liquid impermeable foam member 15b are adhered together by means of an adhesive such as a hot-melt adhesive or the like.

A flat surface part on the underside of liquid impermeable foam member 15b is coupled to the absorber or the surface sheet that covers the absorber (both of which are not shown) in a range wide in the lateral direction by means of an adhesive such as a hot-melt adhesive or the like.

In canal member 14l, since canal sheet 12b is covered by liquid impermeable foam member 15b, the bottom surface part and parts of the left side surface part and right side surface part of the canal part obtain liquid impermeability (leak prevention property), canal sheet 12b is effectively reinforced, the settling phenomenon of the canal part is significantly alleviated, deformation is almost eliminated, and thus, the V-shaped or U-shaped three-dimensional structure can be easily maintained over the area centered around crotch part C, and also, deformation is reduced in the area around crotch part C.

Figure 5G:
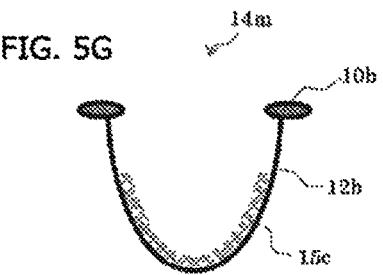
Figure 5H:
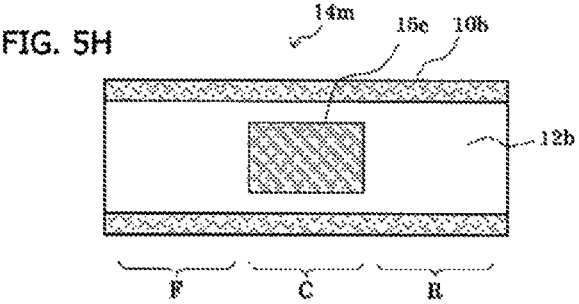

Canal member 14m, shown in FIG. 5(G) and FIG. 5(H), is similar to canal member 14b shown in FIG. 3(A); however, liquid-absorbing foam member 15c (such as a compressively pressed cellulose sponge sheet having, for example, a thickness of 1 mm) is provided on the upper side (the inner side) of canal sheet 12b (such as a hydrophobic non-woven fabric (for example, a PP SMMS non-woven fabric)).

Liquid-absorbing foam member 15c is provided at crotch part C of canal member 14k in the front-rear direction and is provided so as to cover the bottom surface and parts of the left side surface part and right side surface part of the canal part in the lateral direction. Canal sheet 12b and liquid-absorbing foam member 15c are adhered together by means of an adhesive such as a hot-melt adhesive or the like.

In canal member 14m, since canal sheet 12b is covered by liquid-absorbing foam member 15c, the bottom surface and parts of the left side surface part and right side surface part obtain hydrophilicity on the inner surfaces of the canal part, the wettability with respect to bodily fluids becomes prominent, the shifting of bodily fluids becomes smooth, canal sheet 12b is effectively reinforced, the settling phenomenon of the canal part is significantly alleviated, deformation is almost eliminated, and thus, the V-shaped or U-shaped three-dimensional structure can be easily maintained over the area centered around crotch part C, and also, deformation is reduced in the area around crotch part C.

Figure 5I:
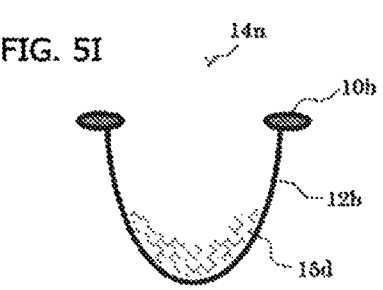
Figure 5J:
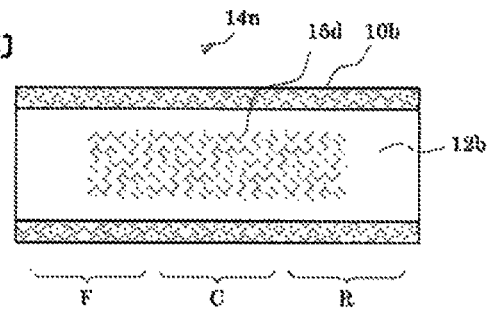

Canal member 14n, shown in FIG. 5(I) and FIG. 5(J), is similar to canal member 14b shown in FIG. 3(A); however, hydrophilic bulky web 15d (such as a surface-hydrophilized PET fiber web (for example, a bulky web obtained by lightly needle-punching a carded web (having a basis weight of 50 g/m$^2$) of a hollow PET fiber (for example, having 7 denier))) is provided on the upper side (the inner side) of canal sheet 12b (such as a hydrophobic non-woven fabric (for example, a PP SMMS non-woven fabric)). Hydrophilic bulky web 15d fills approximately one third of the internal volume of the canal part.

Hydrophilic bulky web 15d is provided over crotch part C and parts of front body F and rear body R of canal member 14n in the front-rear direction, and is provided so as to cover the bottom surface part and parts of the left side surface part and right side surface part of the canal part in the lateral direction. Canal sheet 12b and hydrophilic bulky web 15d are adhered together by means of an adhesive such as a hot-melt adhesive or the like.

In canal member 14n, since canal sheet 12b is covered by hydrophilic bulky web 15d and is filled thereby, the bottom surface and parts of the left side surface part and right side surface part obtain hydrophilicity on the inner surfaces of the canal part, the wettability with respect to bodily fluids becomes prominent, the shifting of bodily fluids becomes smooth, canal sheet 12b is effectively reinforced, the settling phenomenon of the canal part is significantly alleviated, deformation is almost eliminated, and thus, the V-shaped or U-shaped three-dimensional structure can be easily maintained over the area centered around crotch part C, and also, deformation is reduced in the area around crotch part C.

3. Configuration of Fixing Member and its Relationship with Canal Member

An S-part includes a canal member and a fixing member.

The fixing member is not particularly limited, as long as it fixes the canal member to the wearer's body at the time of wearing such that the head parts of the canal member make contact with the wearer's skin.

Examples of materials used for the fixing member include a non-woven fabric and a multilayered sheet in which a non-woven fabric and a liquid impermeable film (for example, air-permeable PE film) are laminated together.

Among such materials, at least part of the fixing member is preferably liquid impermeable. In this case, even when the bodily fluid flows to the end part of the canal member, it is still possible to prevent the bodily fluid from leaching and leaking to the outside.

The configuration of the fixing member is not particularly limited. The S-part may be obtained by coupling and integrating a fixing member and a canal member together, each being a separate member (separate body coupling type), or the S-part may be obtained by a one-piece member in which a fixing member and a canal member are continuous with each other (continuous integration type).

FIG. 6 contains schematic plan views illustrating various S-parts SP.

Figure 6A:
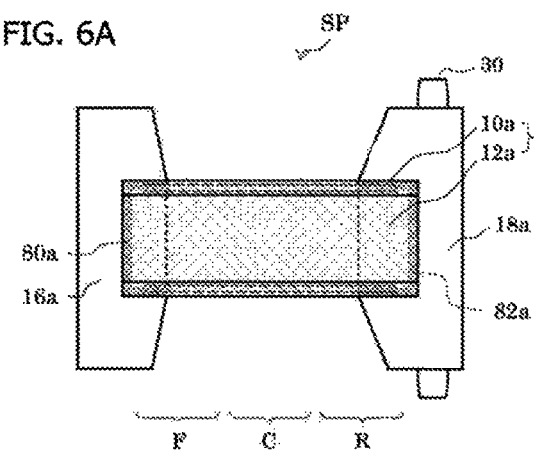
Figure 6B:
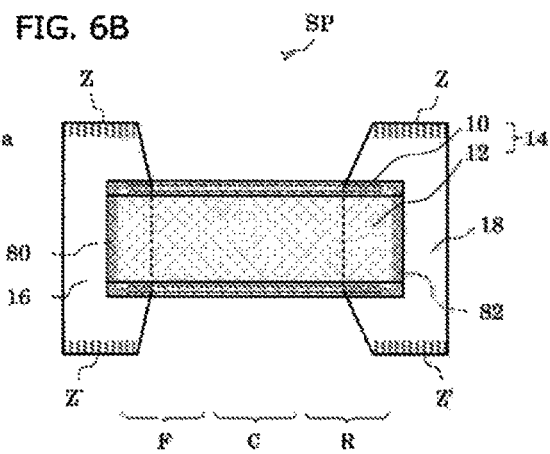

FIG. 6(A) and FIG. 6(B) respectively show an S-part SP of a separate body coupling type.

The S-part SP shown in FIG. 6(A) is the same as that shown in FIG. 2(A). The S-part SP shown in FIG. 6(A) is, as described above, used for an absorbent article in the form of a tape-type diaper.

The S-part SP is configured by coupling and integrating front covering-part 16a and rear covering-part 18a, which function as fixing members, and canal member 14a together.

Detachable members 30 are provided on both the right and left sides of rear covering-part 18a. Detachable members (not shown) are also provided on the under surface of front covering-part 16a, such that they can be detached from detachable members 30.

The S-part SP shown in FIG. 6(B) is the same as that of absorbent article 100 shown in FIG. 1 (however, FIG. 6(B) is simplified). The S-part SP shown in FIG. 6(B) is, as described above, used for the absorbent article in the form of a pants-type diaper.

The S-part SP is configured by coupling and integrating front covering-part 16 and rear covering-part 18, which function as fixing members, and canal member 14 together.

Abdominal sealing parts Z and abdominal sealing parts Z' of the right and left edge parts of front covering-part 16 and rear covering-part 18 are coupled to each other, respectively. This coupling may be carried out prior to, after or simultaneously with integration with canal member 14.

Front covering-part 16 and rear covering-part 18 may be produced by cutting them out from one raw material.

Figure 6C:
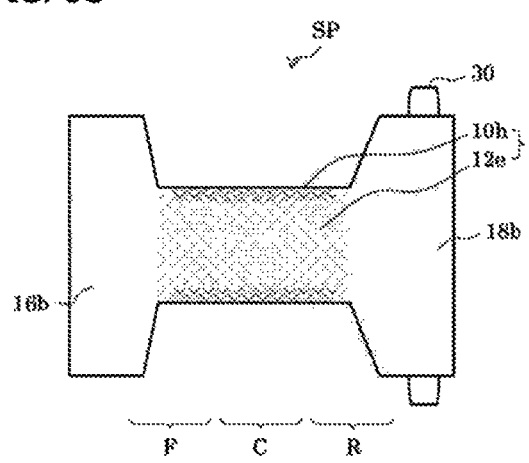
Figure 6D:
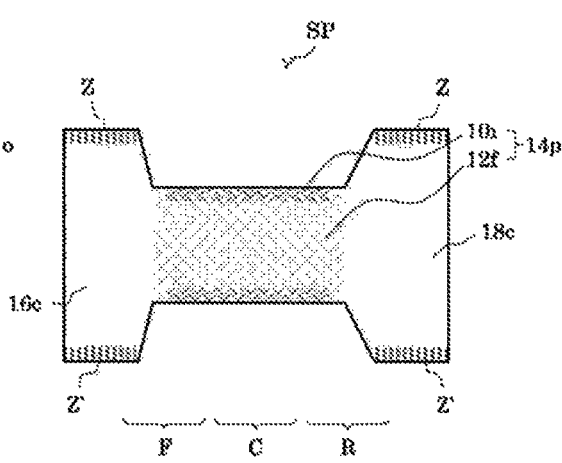

FIG. 6(C) and FIG. 6(D) respectively show an S-part SP of a continuous integration type S-part SP shown in FIG. 6(C) is used for an absorbent article in the form of a tape-type diaper.

In S-part SP shown in FIG. 6(C), canal member 14o includes head parts 10h and canal sheet 12e. Canal sheet 12e is configured by a one-piece member (for example, a non-woven fabric) in continuous with front covering-part 16b and rear covering-part 18b. Head parts 10h are provided by coupling stretchable bodies to the right and left edge parts of such member.

Detachable members 30 are provided on both the right and left sides of rear covering-part 18b. Detachable members (not shown) are also provided on the under surface of front covering-part 16b, such that they can be detached from detachable members 30.

S-part SP shown in FIG. 6(D) is used for an absorbent article in the form of a pants-type diaper.

In S-part SP shown in FIG. 6(D), canal member 14p includes head parts 10i and canal sheet 12f. Canal sheet 12f is configured by a one-piece member (for example, a non-woven fabric) in continuous with front covering-part 16c and rear covering-pan 18c. Head parts 10i are provided by coupling stretchable bodies to the right and left edge parts of such member.

Abdominal sealing parts Z of the right and left edge parts of front covering-part 16b are coupled to each other and abdominal sealing parts Z' of the right and left edge parts of rear covering-part 18b are coupled to each other.

Figure 6E:
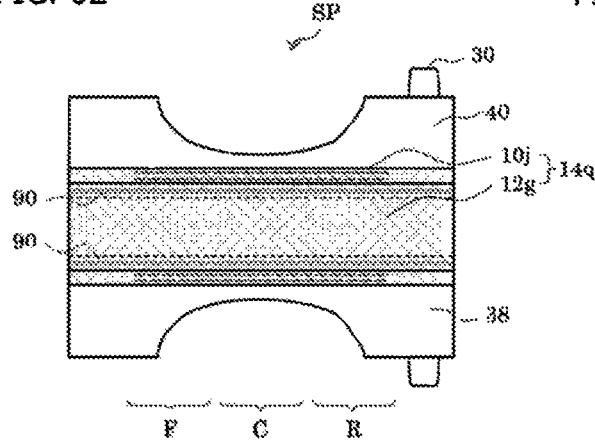
Figure 6F:
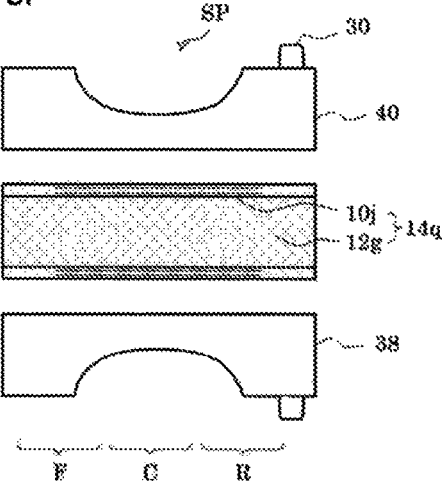

FIG. 6(E) shows an S-part of a separate body coupling type. FIG. 6(F) shows a plurality of members that configure the S-part shown in FIG. 6(E).

S-part SP shown in FIG. 6(E) is used for an absorbent article in the form of a tape-type diaper.

S-part SP shown in FIG. 6(E) is configured by canal member 14q, which includes a pair of right and left head parts 10j and canal sheet 12g shown in FIG. 6(F), and left side covering part 38 and right side covering part 40, which function as fixing members.

As shown in FIG. 6(E), left side covering part 38 and right side covering part 40 are respectively coupled and, thus, integrated on the left side of canal member 14q and on the right side of canal member 14q at coupling parts 90. Front body F parts of left side covering part 38 and right side covering part 40 may be considered as the front covering-part, and rear body R parts thereof may be considered as the rear covering-part.

Detachable members 30 are respectively provided on the rear left side of left side covering part 38 and on the rear right side of right side covering part 40. Detachable members (not shown) are also respectively provided on the under surfaces of left side covering part 38 and right side covering part 40, such that they can be detached from detachable members 30.

Left side covering part 38 and right side covering part 40 may be produced by cutting them out from one raw material.

4. Configuration of R-Part

FIG. and FIG. 8 respectively contain schematic diagrams illustrating various R-parts.

Figure 7A:
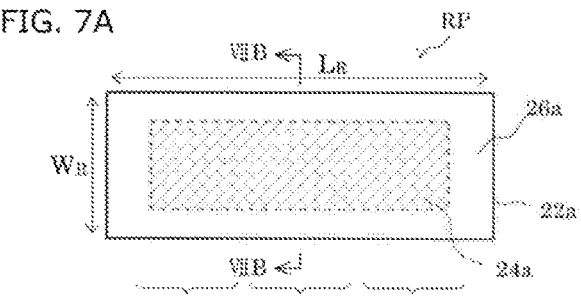
Figure 7B:
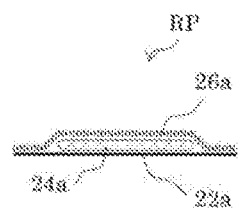

FIG. 7(A) is a plan view of an R-part. FIG. 7(B) is a lateral end view along line VIIB-VIIB in FIG. 7(A).

The R-part shown in FIG. 7(A) and FIG. 7(B) includes leak preventer 22a in sheet form, absorber 24a and surface sheet 26a.

Absorber 24a is arranged above liquid impermeable leak preventer 22a in a continuous manner from front body F to rear body R via crotch part C, and the entire upper surface thereof is covered by liquid permeable surface sheet 26a.

Leak preventer 22a and surface sheet 26a are coupled together at rear, front, right and left edge parts such that absorber 24a is prevented from leaking or sticking out to the outside.

The size of the R-part shown in FIG. 7(A) is not particularly limited.

Length (total length) LR in the front-rear direction of the R-part has a larger margin of choice as compared to total length Ls of the S-part.

Total length LR of the R-part may be shorter or longer than total length LS of the S-part, and it may be shorter or longer than total length LC of the canal member.

Width (total width) WR in the lateral direction of the R-part has a larger margin of choice as compared to total width WS of the S-part.

Total width WR of the R-part may be shorter or longer than total width WS of the S-part, or it may be shorter or longer than total width WC of the canal member. For example, total width WS of the S-part may be longer than total width WC of the canal member, and total width WR of the R-part may be longer than total width WS of the S-part.

The R-part shown in FIG. 7(I) and FIG. 7(J), which will be described hereinafter, is an example in which it has total length LR which is relatively short and total width WR which is relatively long.

According to the present invention, the leak preventer is not particularly limited, as long as it is a leak preventer in sheet form and prevents bodily fluid leakage.

Materials that are generally used as a back sheet can be used for the materials of the leak preventer. In particular, a resin film made of, for example, PE, PP, PET, EVA or the like and a bodily liquid impermeable sheet such as a foam sheet made of the resin described above can be used. For the bodily liquid impermeable sheet, a sheet having air permeability, such as an air permeable sheet or the like may also be preferably used.

In addition, when the above-described resin film is used, a multilayered sheet of such film and a non-woven fabric may be used in order to improve the texture and appearance. In this case, a spunbonded (SB) or thermalbond non-woven fabric having a relatively low basis weight (for example, an air-through type) or the like may be preferably used as the non-woven fabric.

Moreover, a multilayered sheet of such resin film and an absorber in sheet form, which is described below, may also be used.

Further, a high water-resistant non-woven fabric may also be used. Examples of such high water-resistant non-woven fabric include an SMS non-woven fabric having a degree of water resistance of 100 mm H2O or more and an SMS non-woven fabric in which pores in a non-woven web are filled with microfibrillated cellulose (MFC) or wax so as to provide such fabric with water resistance. In this case, a high water-resistant non-woven fabric may be used alone or may also be used as a multilayered sheet of the film and such high water-resistant non-woven fabric.

The leak preventer may be configured from a plurality of members.

The leak preventer is in sheet form; however, it is not particularly limited in terms of shape, as long as it envelops the absorber, or the like, above itself.

The absorber used in the present invention is not particularly limited, as long as it is capable of absorbing bodily fluids, and any absorber used in publicly known conventional absorbent articles may be used. Examples such as: pulverized wood pulp; an absorber in which pulverized wood pulp and granular or powdery SAP are mixed and shaped into a mat; a sheet-like absorber formed into a thin sheet and having SAP as a primary component, or the like, may be used. To keep the shape of these absorbers and at the same time to prevent the generation and droppage of fine powder generating from pulp and SAP, these absorbers are, in general, covered with a core wrapping material made of tissue paper, a non-woven fabric, a perforated film, or the like. In the present specification, when a core wrapping material is used, such core wrapping material is also inclusively referred to as an "absorber."

An absorber in sheet form excels in morphological stability and capability of SAP fall prevention, etc.

Among various types of absorber in sheet form, a super absorbent sheet containing 50 mass % or more, preferably 60 mass % or more, or more preferably 70 mass % or more of SAP is preferred. In addition, from the perspective of stability, etc. of the super absorbent sheet, the content of SAP therein is preferably 95 mass % or less.

The super absorbent sheet is an extremely-thin absorber in sheet form having SAP as a primary component. Since the content of SAP is extremely high, the thickness of the super absorbent sheet is extremely low. The thickness of the super absorbent sheet is preferably 1.5 mm or less and more preferably 1 mm or less.

The super absorbent sheet is not particularly limited in terms of its configuration and production method, as long as it is an extremely-thin absorber in sheet form having SAP as a primary component.

For example, there is a super absorbent sheet obtained by an Air-Laid process. In the Air-Laid process, pulverized wooden pulp and SAP are mixed and a binder is added to shape the mixture into a sheet form and then a super absorbent sheet is obtained. As examples of a super absorbent sheet obtained through this process, NOVATHIN (US trademark) manufactured by Rayonier Inc. in the US and B-SAP manufactured by Oji Kinocloth Co., Ltd. are known.

Another example of the super absorbent sheet includes a super absorbent sheet obtained through a process involving coating a bodily liquid permeable sheet such as a non-woven fabric with SAP-dispersed slurry. Here, the SAP-dispersed slurry is preferably prepared by dispersing SAP and microfibrillated cellulose (MFC) in a mixed solvent of water and ethanol. As an example of the super absorbent sheet obtained through this process, MegaThin (trademark) manufactured by Japan Absorbent Technology Institute is known.

Other examples of the super absorbent sheet include: a super absorbent sheet obtained through a process involving having a raised non-woven fabric carry a large amount of SAP and fixing the SAP with a hot melt binder, an emulsion binder, a water-soluble fiber, or the like; a super absorbent sheet obtained through a process involving mixing fibrous SAP with a PET (polyethylene terephthalate) fiber and forming the mixture into a web; and an SAP sheet obtained by sandwiching an SAP layer with tissues from above and below.

At least one layer of the absorber is arranged above the leak preventer. Namely, the absorber may be comprised of one layer or two or more layers (multilayer).

In addition, the absorber may be arranged in a folded condition.

According to the present invention, the R-part may further include a surface sheet. As for the surface sheet, any surface sheet used as a top sheet in the conventional absorber product may be used; however, a skin-care capability, such as an antibiotic property or the like, may be provided. In addition, a special skin contact sheet, such as that proposed by the present inventor in WO2002/000154, may also be used.

Figure 7C:
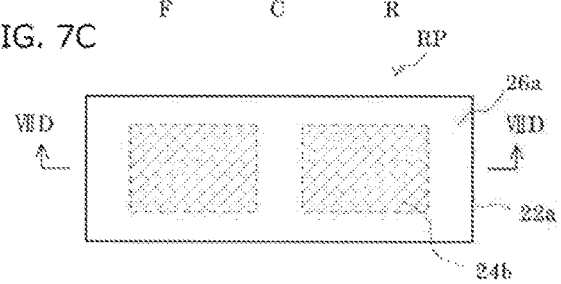
Figure 7D:
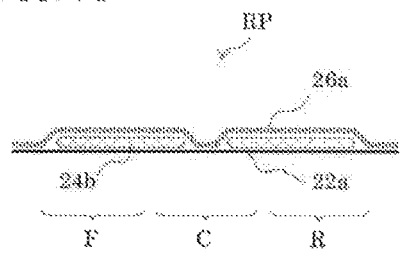

FIG. 7(C) is a plan view of an R-part in another form. FIG. 7(D) is a longitudinal end view along line VIID-VIID in FIG. 7(C).

The R-part, shown in FIG. 7(C) and FIG. 7(D), is similar to the R-part, shown in FIG. 7(A) and FIG. 7(B); however, it differs therefrom with respect to the point that it includes, instead of absorber 24a, two absorbers 24b which are present in the front part and the rear part.

Leak preventer 22a and surface sheet 26a are coupled together in the section in the center part in the front-rear direction, where absorbers 24b are not present.

The R-part in this form has the advantage that it may be easily folded in the front-rear direction with the center part without any absorber serving as the folding line.

Figure 7E:
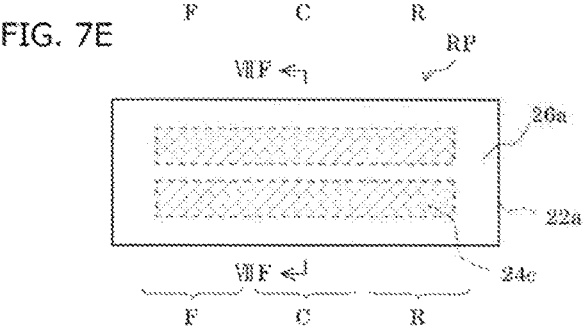
Figure 7F:
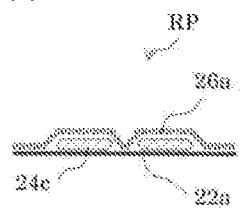

FIG. 7(E) is a plan view of an R-part in a further form. FIG. 7(F) is a lateral end view along line VIIF-VIIF in FIG. 7(E).

The R-part shown in FIG. 7(E) and FIG. 7(F) is similar to the R-part shown in FIG. 7(A) and FIG. 7(B); however, it differs therefrom with respect to the point that it includes, instead of absorber 24a, two elongated absorbers 24c which are present on both the right and left sides.

Leak preventer 22a and surface sheet 26a are coupled together in the section in the center part in the lateral direction, where absorbers 24c are not present.

The R-part in this form has the advantage that it may be easily folded in the lateral direction with the center part without any absorber serving as the folding line.

Figure 7G:
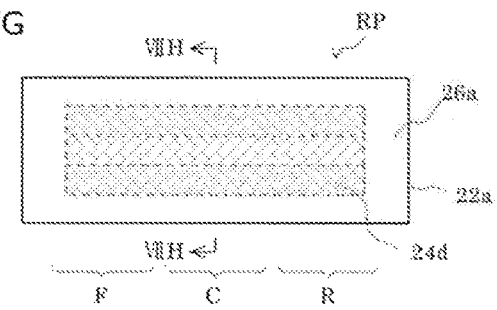
Figure 7H:
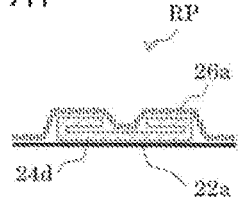

FIG. 7(G) is a plan view of an R-part in a further form. FIG. 7(H) is a lateral end view along line VIIH-VIIH in FIG. 7(G).

The R-part, shown in FIG. 7(G) and FIG. 7(H), is similar to the R-part, shown in FIG. 7(A) and FIG. 7(B); however, it differs therefrom with respect to the point that it includes, instead of absorber 24a, absorber 24d in which both the right and left edge parts are folded back to the upper side and thus, the center part consists of one layer and both the right and left sides thereof consist of two layers.

The R-part in this form has the advantage that it may be easily folded in the lateral direction with the center part, in which the absorber consists of one layer, serving as the folding line.

Figure 7I:
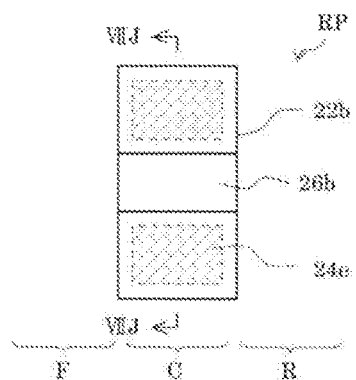

FIG. 7(I) is a plan view of an R-part in a further form. FIG. 7(J) is a lateral end view along line VIIJ-VIIJ in FIG. 7(I).

Figure 7J:
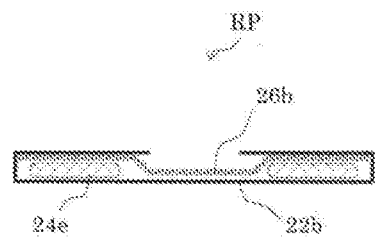

The R-part shown in FIG. 7(I) and FIG. 7(J) includes leak preventer 22b in sheet form, two absorbers 24e and surface sheet 26b.

Leak preventer 22b in sheet form has a relatively short length in the front-rear direction (for example, 100 to 150 mm) and it is present substantially at only crotch part C.

Leak preventer 22b in sheet firm has a relatively wide width in the lateral direction (for example, approximately 200 mm) and it extends in the lateral direction in a wing-like fashion.

For each of the two absorbers 24e, for example, a rectangular absorber (for example, having a length of 100 min and a width of 50 mm) is used and they are arranged on both the right and left sides of leak preventer 22b. The entire upper surface thereof is covered by liquid permeable surface sheet 26b and further, the upper side thereof is covered by leak preventer 22b having the right and left edge parts thereof being folded back to the upper side. No absorber is present in the center part in the width direction of leak preventer 22b.

Leak preventer 22b and surface sheet 26b are coupled together at the front and rear end parts.

Leak preventer 22b forms a bag-like capsule in which absorber 24e is arranged: by covering three surfaces of the left absorber 24e, i.e. the under surface, the left side surface and the upper surface thereof; and by coupling the folded-back parts to each other at the edge parts where absorber 24e is not present on the front and rear sides of the left absorber 24e. Similarly, leak preventer 22b forms a bag-like capsule in which absorber 24e is arranged: by covering three surfaces of the right absorber 24e, i.e. the under surface, the right side surface and the upper surface thereof; and by coupling the folded-back parts to each other at the edge parts where absorber 24e is not present on the front and rear sides of the right absorber 24e.

The capsules on both the right and left sides have opposing opening parts. These opening parts constitute points of access for bodily fluids transferred from the canal part.

Figure 8A:
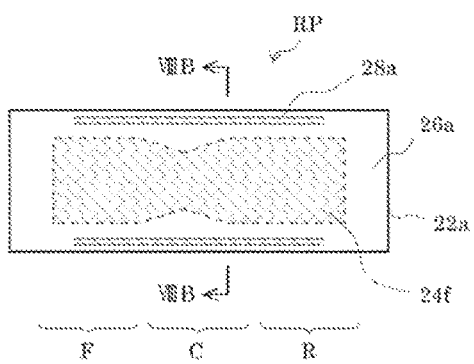
Figure 8B:
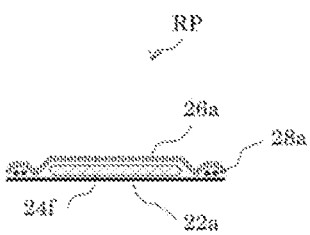

FIG. 8(A) is a developed plan view of the state (tension state) in which stress is applied to an R-part in another form such that it is pulled in the front-rear direction and the lateral direction in order to be developed into a substantially planar form. FIG. 8(B) is a lateral end view along line VIIIB-VIIIB in FIG. 8(A).

The R-part shown in FIG. 8(A) and FIG. 8(B) includes leak preventer 22a in sheet form, absorber 24f and surface sheet 26a.

Absorber 24f has a shape in which the center part in the front-rear direction is dented and is arranged above liquid impermeable leak preventer 22a in a continuous manner from front body F to rear body R via crotch part C. The entire upper surface thereof is covered by liquid permeable surface sheet 26a.

The R-part in this form has the advantage that it may be easily folded in the front-rear direction with the center part, where the width in the lateral direction of the absorber is narrowed, serving as the folding line.

Leak preventer 22a and surface sheet 26a are coupled together at rear, front, right and left edge parts such that absorber 24a is prevented from leaking or sticking out to the outside.

Two filament-like stretchable members 28a are provided, sandwiched between leak preventer 22a and surface sheet 26a, at the right and left edge parts of leak preventer 22a, and more specifically at the coupling parts of the right and left end parts between leak preventer 22a and surface sheet 26a.

Stretchable member 28a is not intended to prevent side leakage of bodily fluids by being closely attached to the wearer's body, as seen in an inner leg gather (ILG) or an outer leg gather (OLG) in the conventional absorbent articles. Rather, it is intended to increase the contact area between the surface of the R-part and the curved surface of the bottom surface part of the canal part, by allowing deformation and rising in convex form (i.e. a C-shape) to the underside through the provision of an effect of contracting the length in the front-rear direction of the stretchable member.

As described above, the leak preventer having stretchable members on the right and left edge parts thereof for providing an effect of decreasing the length in the front-rear direction of the members is one of the preferred embodiments of the absorbent article according to the present invention.

In addition, as described above, the leak preventer assuming a convex shape on the underside at at least the crotch part at the time of wearing is one of the preferred embodiments of the absorbent article according to the present invention.

Figure 8C:
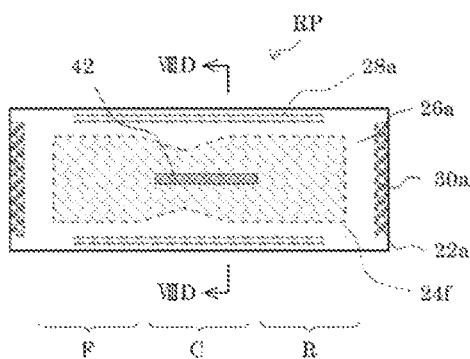
Figure 8D:
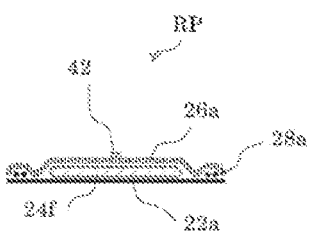

FIG. 8(C) is a developed plan view of the state (tension state) in which stress is applied to an R-part in another form such that it is pulled in the front-rear direction and the lateral direction in order to be developed into a substantially planar form. FIG. 8(D) is a lateral end view along line VIIID-VIIID in FIG. 8(C).

The R-part shown in FIG. 8(C) and FIG. 8(D) is similar to the R-part shown in FIG. 8(A) and FIG. 8(B); however, it differs therefrom with respect to the point that it includes detachable members 30a, which respectively couple the S-part (not shown) and the R-part in a detachable manner at the front and rear end parts of surface sheet 26a and the point that it further includes adhesive member 42, which extends in the front-rear direction and allows coupling to the bottom surface part of the canal part in a detachable manner at the center part in the lateral direction of crotch part C of surface sheet 26a.

For detachable members 30a, a detachable member the same as detachable member 30 may be used. These detachable members may be configured by, for example, various hook-and-loop fasteners. In particular, as for detachable members 30a, adhesive tape or Velcro tape (male) may be used. As for the detachable members provided on the S-part, tape landing zones (TLZs) (female) or zipper landing zones (ZLZs) (female) may be used.

Adhesive member 42 is preferably covered by a paper liner prior to use.

The R-part shown in FIG. 8(C) and FIG. 8(D) is made detachable from the S-part by the effect of detachable members 30a and adhesive member 42.

As described above, the S-part and the R-part being detachable is one of the preferred embodiments of the absorbent article according to the present invention.

Figure 8E:
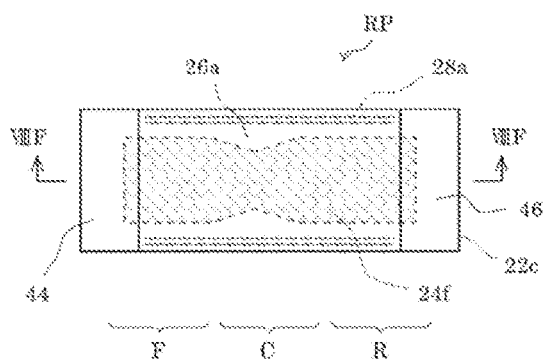
Figure 8F:
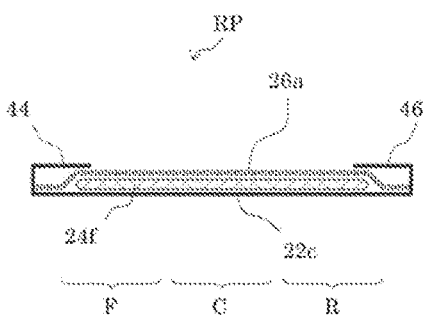

FIG. 8(E) is a developed plan view of the state (tension state) in which stress is applied to an R-part in a further form such that is pulled in the front-rear direction and the lateral direction in order to be developed in a substantially planar form. FIG. 8(F) is a longitudinal end view along line VIIF-VIIF in FIG. 8(E).

The R-part, shown in FIG. 8(E) and FIG. 8(F), is similar to the R-part, shown in FIG. 8(A) and FIG. 8(B); however, it differs therefrom with respect to the point that front pocket part 44 and rear pocket part 46 are formed by leak preventer 22c being folded back to the upper side at the front and rear end parts thereof and the right and left edge parts of the folded-back parts being coupled to surface sheet 26a.

The R-part in this form can effectively suppress the generation of front and rear leakage by means of front pocket part 44 and rear pocket part 46.

5. Coupling State Between Part of Under Surface of Canal Sheet of S-Part and Part of Surface of Absorber (or Surface Sheet or Diffusion Sheet Covering Absorber) of R-Part According to the absorbent article of the present invention, part of the under surface of the canal sheet of the S-part and part of the surface of the absorber (or the surface sheet or diffusion sheet covering the absorber) of the R-part, at least, are coupled together. In this way, it is possible to smoothly transfer bodily fluids received in the canal part onto the surface of the absorber via a passage.

FIG. 9 and FIG. 10 contain schematic lateral end views illustrating various absorbent articles, according to the present invention, at crotch part C.

Figure 9A:
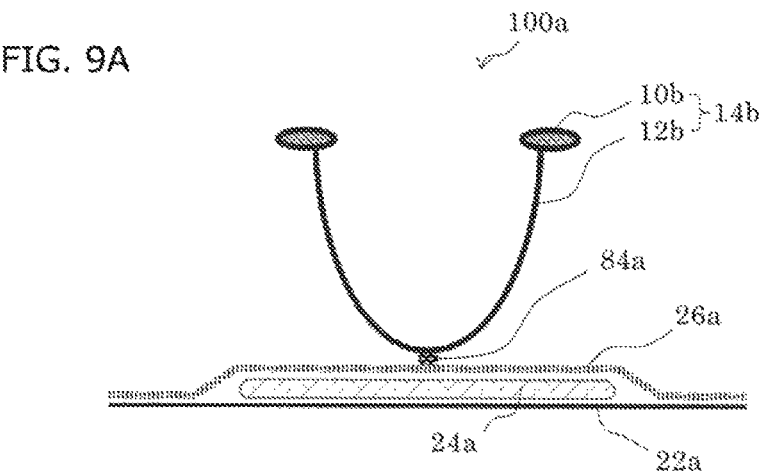

Absorbent article 100a shown in FIG. 9(A) includes an S-part having canal member 14v shown in FIG. 3(A) and an R-part shown in FIG. 7(A) and FIG. 7(B).

The under surface of canal sheet 12b of the S-part and the surface of surface sheet 26a covering absorber 24a of the R-part are coupled together, at the center part in the lateral direction, by means of bottom surface coupling part 84a that extends in the front-rear direction.

As described above, part of the center part in the lateral direction of the under surface of the canal sheet and part of the surface of the absorber or the surface sheet covering the absorber being coupled together at the bottom surface coupling part, is one of the preferred embodiments of the absorbent article according to the present invention.

Bottom surface coupling part 84a has a linear shape with a narrow width in the lateral direction. However, it may have a belt-like form with a wide width in the lateral direction.

Bottom surface coupling part 84a may be present only at crotch part C, or it may extend to front body F and/or rear body R from crotch part C. The bottom surface coupling part extending in the front-rear direction in the area including crotch part C is one of the preferred embodiments of the absorbent article according to the present invention.

Figure 9B:
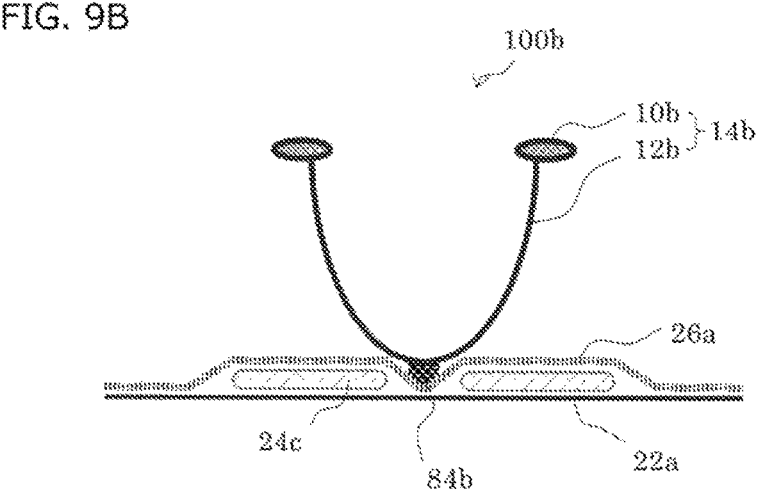

Absorbent article 100b shown in FIG. 9(B) includes an S-part having canal member 14b shown in FIG. 3(A) and an R-part shown in FIG. 7(E) and FIG. 7(F).

The under surface of canal sheet 12b of the S-part and the surface of surface sheet 26a covering absorber 24c of the R-part are coupled together, at the center part in the lateral direction (where absorber 24c is not present), by means of bottom surface coupling part 84b that linearly extends in the front-rear direction.

Bottom surface coupling part 84b has a linear shape with a narrow width in the lateral direction. However, it may have a belt-like form with a wide width in the lateral direction.

Bottom surface coupling part 84b may be present only at crotch part C, or it may extend to front body F and/or rear body R from crotch part C.

Figure 9C:
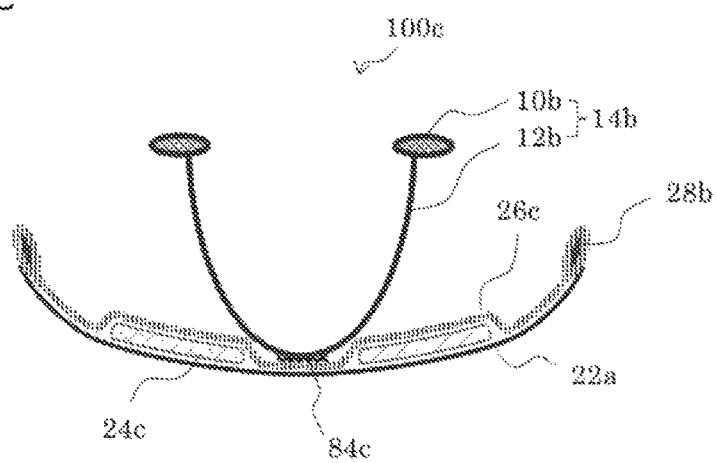

Absorbent article 100c shown in FIG. 9(C) is similar to absorbent article 100b shown in FIG. 9(B); however, surface sheet 26c is folded back to the underside at the right and left edge parts thereof and covers stretchable members 28b. Since stretchable members 28b have a function similar to that of the above-described stretchable members 28a, bottom surface coupling part 84c can be easily made into a belt-like form with a wide width in the lateral direction.

Bottom surface coupling part 84c has a belt-like form with a wide width in the lateral direction. However, it may have a linear shape with a narrow width in the lateral direction.

Bottom surface coupling part 84c may be present only at crotch part C, or it may extend to front body F and/or rear body R from crotch part C.

Figure 10A:
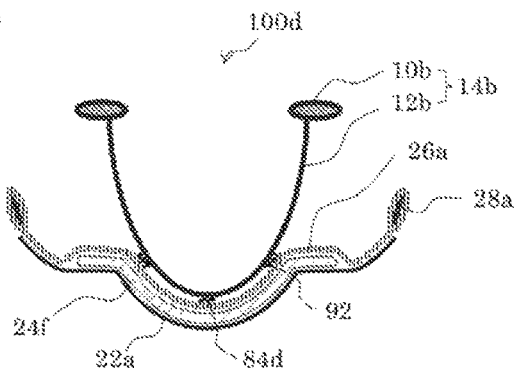

Absorbent article 100d shown in FIG. 10(A) includes an S-part having canal member 14b shown in FIG. 3(A) and an R-part shown in FIG. 8(A) and FIG. 8(B).

The under surface of canal sheet 12b of the S-part and the surface of surface sheet 26a covering absorber 24f of the R-part are coupled together, at the center part in the lateral direction and on both the right and left sides thereof, at three locations, i.e. bottom surface coupling part 84d that extends in the front-rear direction and both side surface coupling parts 92.

In the absorbent article of this form, the R-part is deformed and rises in convex form (i.e. a C-shape) to the underside so as to fit to the V-shape or U-shape of the canal part, and thus, it couples to and reinforces the part of the canal part from the bottom surface to the side surface. Thereby, the three-dimensional structure of the canal part is easily maintained, and the collapsing or deformation of the canal part due to the change in body position or movement of the wearer is significantly suppressed.

As described above, in addition to part of the center part in the lateral direction of the under surface of the canal sheet, parts of the vicinities of the right and left edge parts of the under surface of the canal sheet and parts of the surface of the absorber or the surface sheet, etc. covering the absorber being coupled together with the right and left side surface coupling parts, is one of the preferred embodiments of the absorbent article according to the present invention.

Side surface coupling parts 92 may be present only at crotch part C, or they may extend to front body F and/or rear body R from crotch part C. The side surface coupling part extending in the front-rear direction in the area including crotch part C is one of the preferred embodiments of the absorbent article according to the present invention.

In the absorbent article of this form, the under surface of canal sheet 12b of the S-part and the surface of surface sheet 26a covering absorber 24a are coupled together at three locations; however, they may be coupled together in a continuous manner from the bottom surface to the side surfaces of the canal part.

With the absorbent article including such side surface coupling parts, the form which is convex to the underside can be easily formed at the time of wearing, and in particular, the size of the form which is convex to the underside becomes large at the crotch part.

Figure 10B:
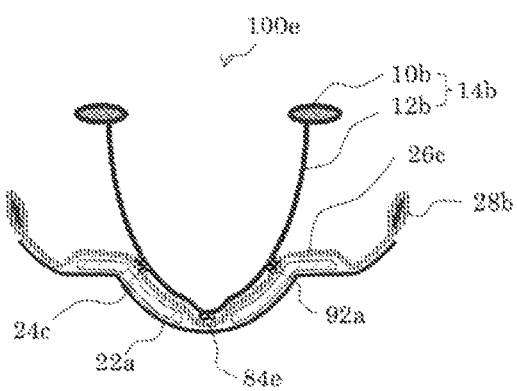

Absorbent article 100e shown in FIG. 10(B) is similar to absorbent article 100c shown in FIG. 9(C); however, it differs therefrom with respect to the point that the under surface of canal sheet 12b of the S-part and the surface of surface sheet 26c covering absorber 24c of the R-part are coupled together, at the center part in the lateral direction and on both the right and left sides thereof, at three locations, i.e. bottom surface coupling part 84e that extends in the front-rear direction and both side surface coupling parts 92a.

The effect of coupling at three locations is similar to that of absorbent article 100d shown in FIG. 10(A).

In absorbent article 10e shown in FIG. 10(B), since no absorber is present at the center part in the lateral direction, folding in the lateral direction is easy. Thus, the cross-sectional shape of the canal part is close to a V-shape as compared to absorbent article 100d shown in FIG. 10(A), which assumes a shape close to a U-shape.

In the absorbent article of this form, the under surface of canal sheet 12b of the S-part and the surface of surface sheet 26c covering absorber 24c are coupled together at three locations; however, they may be coupled together in a continuous manner from the bottom surface to the side surfaces of the canal part.

Figure 10C:
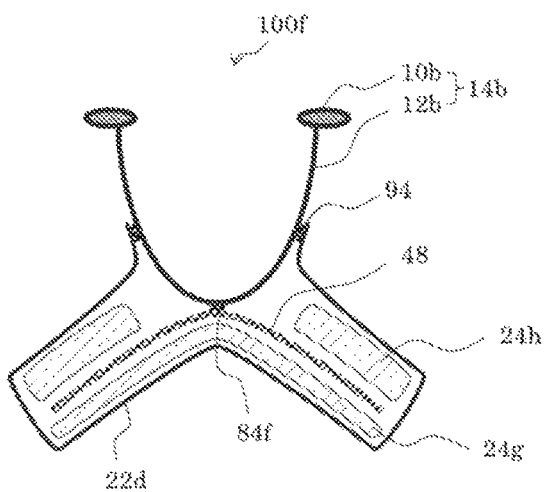

Absorbent article 100f shown in FIG. 10(C) includes an S-part having canal member 14 shown in FIG. 3(A) and an R-part having capsules on both the right and left sides.

Absorber 24g, which extends over the entire area in the lateral direction above leak preventer 22d, diffusion sheet 48 which covers absorber 24g, and two absorbers 24h, which are present on both the right and left sides of diffusion sheet 48, are provided in the R-part.

Leak preventer 22d in sheet form has a relatively short length in the front-rear direction (for example, approximately 120 mm) and it is present substantially only at crotch part C.

Leak preventer 22b in sheet form has a relatively wide width in the lateral direction (for example, approximately 300 mm) and it extends in the lateral direction in a wing-like fashion.

For each of the two absorbers 24h, for example, a rectangular absorber (for example, having a length of 100 mm and a width of 50 mm) is used.

Leak preventer 22d is folded back to the upper side at the right and left edge parts thereof, the folded-back parts are coupled to each other at front and rear ends thereof (both of which are not shown), and bag-like capsules are formed.

The capsules on both the right and left sides have opposing opening parts. These opening parts constitute points of access for bodily fluids transferred from the canal part.

Diffusion sheet 48 is not particularly limited, as long as it has a configuration having a flow path that allows for movement of urine; however, it is preferred that it does not have bodily fluid absorbability nor bodily fluid retaining capacity, for allowing rapid movement of urine. In particular, a concave-convex sheet member having openings at convex parts (a perforated concave-convex sheet member) may be preferably provided as an example.

The under surface of canal sheet 12b of the S-part and the surface of diffusion sheet 48 covering absorber 24g of the R-part are coupled together, at the center part in the lateral direction, at bottom surface coupling part 84f that extends in the front-rear direction. In addition, the under surface of canal sheet 12 of the S-part and the end parts of the folded-back parts of leak preventer 22d of the R-part are coupled together, on both the right and left sides, at S-part-R-part side edge coupling parts 94 that extend in the front-rear direction. In this way, the S-part and the R-part are coupled and integrated together at three locations in FIG. 10(C).

In addition, although not shown, the front and rear ends of the R-part are partially coupled to the under surface (outer surface) of canal sheet 12b by means of an adhesive such as a hot-melt adhesive or the like.

The absorbent article of a capsule type shown in FIG. 10(C) can receive the excretory organ of the wearer so as to completely cover the same at crotch part C. Accordingly, it is preferably used for, for example, incontinence articles or night-time sanitary napkins for females.

6. Other Coupling States of S-Part and R-Part

According to the absorbent articles of the present invention, from a functional perspective, as described above, it is sufficient when part of the under surface of the canal sheet of the S-part and part of the surface of the absorber (or the surface sheet or the diffusion sheet covering the absorber) of the R-part are coupled together, and thus, the S-part and the R-part may not need to be coupled together in other locations. However, when coupling is made in such other locations, the appearance is improved.

When total length LR of the R-part is longer than total length LS of the S-part, both the right and left side edge parts in the vicinity of the front end and/or rear end of the R-part may be coupled to the fixing member(s) (for example, the front covering-part and/or the rear covering-part) by means of an adhesive.

When total length LR of the R-part is equal to total length LS of the S-part or less, the front end and/or the rear end of the R-part may be coupled to the fixing members of the S-part (for example, the front covering-part and/or the rear covering-part) by means of an adhesive. In such case, the form of coupling is not particularly limited. The coupling may be made at three locations including both the right and left edge parts and the center parts, the coupling may be made in a spot fashion at regular intervals or the coupling may be made to the entire surface in belt-like form. In this case, the coupling need not be made in a liquid-tight manner.

Among the above, when total length LR of the R-part is equal to total length Le of the canal member or less, for example, when the R-part is present only at crotch part C, the front end and the rear end of the R-part may be partially or entirely coupled to the canal sheet in the lateral direction.

7. Transfer of Bodily Fluids

According to the absorbent article of the present invention, a passage is provided for transferring bodily fluids from the upper side of the canal sheet onto the surface of the absorber.

Examples of the passage include: micro-openings which are provided in the canal sheet itself (for example, fine pores in a liquid permeable non-woven fabric when the canal sheet is configured by such liquid permeable non-woven fabric), slits provided in the canal sheet, and cutouts provided in the canal sheet.

When a wearer wearing the absorbent article of the present invention excretes a bodily fluid, the excreted bodily fluid is received on the upper side of the canal sheet. Thereafter, it transfers from the upper side of the canal sheet onto the surface of the absorber through the above-described passage while it shifts in the front-rear direction.

8. Method of Producing Absorbent Article of the Present Invention

The absorbent article of the present invention is not particularly limited in terms of the production method thereof; however, it can be produced by carrying out the process of forming each of the S-part and the R-part and the process of thereafter coupling the S-part and the R-part together.

In this way, by modularizing each of the S-part and the R-part, the production processes are simplified, and thus, the investment cost can be suppressed and the productivity can be improved.

Hereinafter, more specific examples of implementation aspects of the absorbent article of the present invention will be described.

Figure 11A:
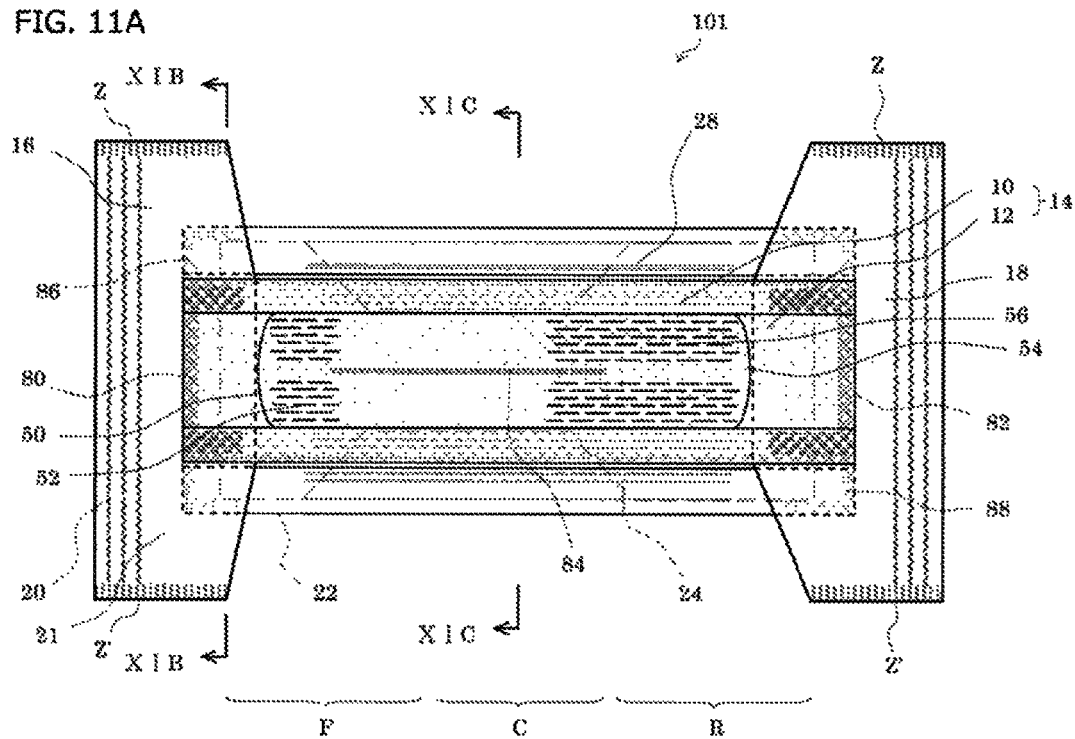
Figure 11B:
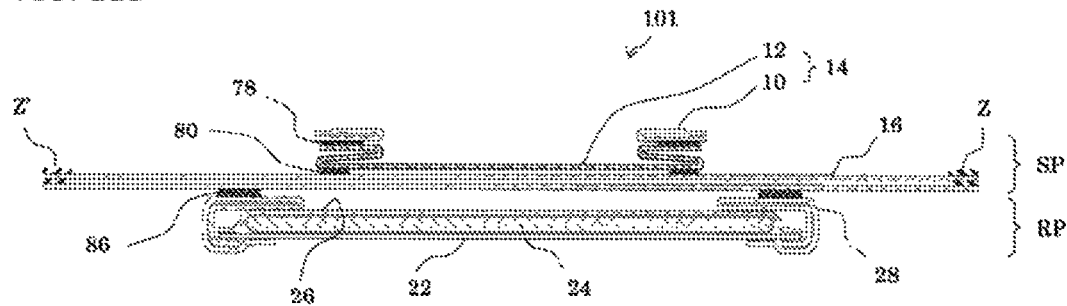
Figure 11C:
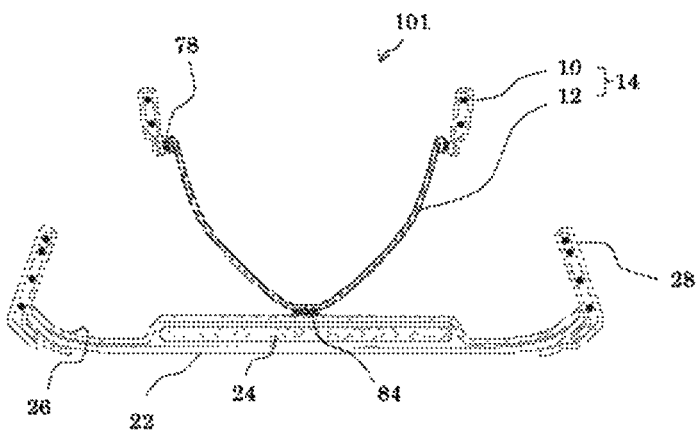

FIG. 11 contains schematic diagrams illustrating another example of an implementation aspect of the absorbent article according to the present invention. FIG. 11(A) is a plan developed view schematically showing the state in which the absorbent article, in the form of a pants-type diaper, is cut at abdominal sealing parts (Z and Z' in FIG. 11(A)) on both the right and left sides of the waist gather thereof, and in which stress is applied to the absorbent article such that it is pulled in the front-rear direction and the lateral direction in order to be developed into a substantially planar form. FIG. 11(B) is a lateral end view along line XIB-XIB in FIG. 11(A). FIG. 11(C) is a lateral end view along line XIC-XIC in FIG. 11(A) when stress is not applied to the absorbent article (relaxed state).

Absorbent article 101 shown in FIG. 11 is similar to absorbent article 100 shown in FIG. 1; however, it differs therefrom with respect to the point that various slits are provided as the passage for transferring the bodily fluid from the upper side of the canal sheet onto the surface of the absorber. Hereinafter, a detailed description will be provided, including the parts that have been omitted when describing absorbent article 100 of the present invention shown in FIG. 1. It should be noted that, in the following description, the materials of the respective members are illustrative.

Absorbent article 101 shown in FIG. 11 is configured as a pants-type diaper for infants (Super Big size (for body weight of approximately 13 to 25 kg)).

The sizes of the respective members of absorbent article 101 described hereinafter are examples in the case of the Super Big size and they can be changed as appropriate. It should also be understood that when the size of the absorbent article is different, the sizes of the respective members will also change.

The sizes of the respective members of absorbent article 101 described hereinafter are the sizes in the tension state, unless otherwise stated.

S-part SP has a total length of 690 mm and a total width of 360 mm (200 mm in the relaxed state).

The canal sheet member has a total length of 550 mm and a total width of 140 mm. Canal sheet 12 has a width of 220 mm when the folded-back parts are unfolded. Each head part in the pair of right and left head parts 10 has a width of 20 mm.

Front covering-part 16 has a total length of 130 mm. Rear covering-part 18 has a total length of 160 mm.

R-part RP has a total length of 550 mm and a total width of 190 mm.

Absorber 24 has an hourglass shape in which the width is narrowed in crotch part C, and has a total length of 490 mm and a total width of 180 mm, at the maximum, and 90 mm, at the minimum.

The S-part is of a separate body coupling type shown in FIG. 6(B).

The under surfaces of the front and rear end parts of canal member 14 and the upper surfaces of front covering-part 16 and rear covering-part 18 are respectively coupled together, in a continuous manner in belt form, at canal part-front end coupling part 80 and canal part-rear end coupling part 82, by means of a hot-melt adhesive, and are therefore integrated together such that a leak prevention property is obtained.

Canal member 14 includes a pair of right and left head parts 10 (which are configured by coupling, in an extended state, the upper surfaces and under surfaces of two polyurethane filaments to a non-woven fabric that serves as a support by means of an adhesive) and hydrophobic canal sheet 12 (which is an SMMS non-woven fabric having a basis weight of 15 g/m$^2$) which connects between the pair of right and left head parts 10.

Since canal sheet 12 is hydrophobic, the fine pores thereof do not provide the function as a passage for transferring a bodily fluid onto the surface of the absorber.

Front part slit 50 in a C-shape, which traverses the front body in the lateral direction, and a group of front slits 52 in fine line form, which are present posterior to front part slit 50 and extend in the front-rear direction, are provided in front body F of canal sheet 12. Front part slit 50 and the group of front slits 52 constitute the passage (front exit) for transferring the bodily fluid from the canal part of the S-part onto absorber 24 of the R-part.

In addition, rear part slit 54 in a C-shape, which traverses the area from rear body R to crotch part C of canal sheet 12 in the lateral direction, and a group of rear slits 56 in fine line form, which are present anterior to rear part slit 54 and extend in the front-rear direction, are provided in such area from rear body R to crotch part C of canal sheet 12. Rear part slit 54 and group of rear slits 56 constitute the passage (rear exit) for transferring the bodily fluid from the canal part of the S-part onto absorber 24 of the R-part.

Each of front covering-part 16 and rear covering-part 18 is configured by two non-woven fabrics (which are PP SMMS non-woven fabrics having a basis weight of 13 g/m$^2$).

Waist gather 20 (which is configured by arranging three pieces of rubber yarn, having a thickness of 0.35 mm and a width of 1 mm, at 12 mm intervals and by sandwiching such rubber yarn between two non-woven fabrics configuring front covering-part 16 and rear covering-part 18) is provided over the entire width in both the vicinities of the front end of front covering-part 16 and the rear end of rear covering-part 18.

Shirring gather 21 (which is configured by arranging three polyurethane filaments having 400 dtex at 20 mm intervals and sandwiching such polyurethane filaments between two non-woven fabrics configuring front covering-part 16 and rear covering-part 18) is provided on both the side posterior to waist gather 20 of front covering-part 16 and the side anterior to waist gather 20 of rear covering-part 18.

Abdominal sealing parts Z, Z' are provided on the right and left edge parts of front covering-part 16 and rear covering-part 18, and the pants-type diaper is formed by coupling abdominal sealing parts Z to each other and by coupling abdominal sealing parts Z' to each other.

The front end of canal member 14 is arranged such that it is located at the position 70 mm posterior to the front end of front covering-part 16. The front end and the right and left side edges around such front end of canal member 14 and the under surface of front covering-part 16 are spot-coupled together by means of a hot-melt adhesive. The rear end of canal member 14 is arranged such that it is located at the position 70 mm anterior to the rear end of rear covering-part 18. The rear end and the right and left side edges around such rear end of canal member 14 and the under surface of rear covering-part 16 are spot-coupled together by means of a hot-melt adhesive.

In the R-part, absorber 24 is arranged on the upper side of leak preventer 22 in sheet form and its upper surface is covered by liquid permeable surface sheet 26. Leak preventer 22 and surface sheet 26 are coupled together on both the right and left edges by means of a hot-melt adhesive so as to prevent absorber 24 from leaking out.

Leak preventer 22 is a laminated body made up of a PE air permeable film having a thickness of 18 μm and a PP/PE spunbonded non-woven fabric having a basis weight of 12 g/m$^2$.

Absorber 24 is an absorber in which a mixture of SAP and pulp (SAP/pulp=60/40 (mass ratio)) is compressed to a thickness of 1.5 mm and which is covered by a tissue having a basis weight of 20 g/m$^2$.

Surface sheet 26 is a PE/PET air-through non-woven fabric having a basis weight of 20 g/m$^2$.

Stretchable members 28 (which are configured by arranging four polyurethane filaments (having a width of 30 mm) in a parallel manner and by covering them with a non-woven fabric) are provided on the right and left edge parts of leak preventer 22. The lower ends of stretchable members 28 on the inner side in the lateral direction are coupled to the under surface of leak preventer 22 and are arranged in a state in which they are folded back onto the upper surface of surface sheet 26.

Stretchable members 28 are for preventing side edge parts of absorber 24 from hanging downward, and stretchable member 28 itself need not make direct contact with the wearer's skin.

As has been described with respect to FIG. 1, between the S-part and the R-part, part of the under surface of canal sheet 12 (i.e. the underside surface of the bottom surface of the canal part configured by canal sheet 12) and part of the surface of absorber 24 (or the surface of surface sheet 26) are coupled together at linear bottom surface coupling part 84 (having a length of 230 mm and a width of 5 mm), which extends from crotch part C to and over front body F, by means of a hot-melt adhesive.

In addition, the under surfaces of front covering-part 16 and rear covering-part 18 of the S-part and the folded-back stretchable members 28 of the R-part are respectively coupled together at R-part-front end coupling part 86 and R-part-rear end coupling part 88.

In this way, the S-part and the R-part are integrated together. The front coupling and rear coupling between the S-part and the R-part play a role of reinforcing the coupling at bottom surface coupling part 84.

As shown in FIG. 11(C), in the relaxed state, the interval between the pair of right and left head parts 10 of canal member 14 of the S-part becomes narrow and the canal part formed by canal sheet 12 is deepened and thus, assumes a V-shape or U-shape.

At the time of wearing absorbent article 101, only the pair of right and left head parts 10 having stretchability at at least part thereof make contact with the wearer's skin, and it is ensured that the R-part including absorber 24 is spaced apart from the wearer's skin.

Figure 12A:
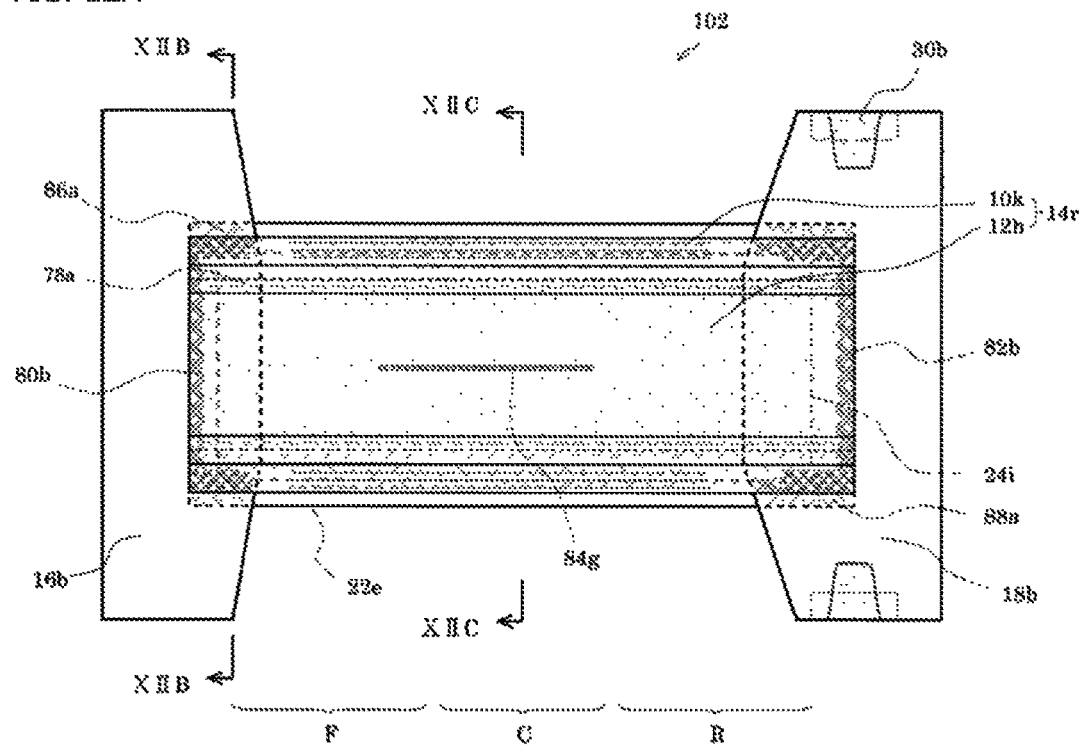
Figure 12B:
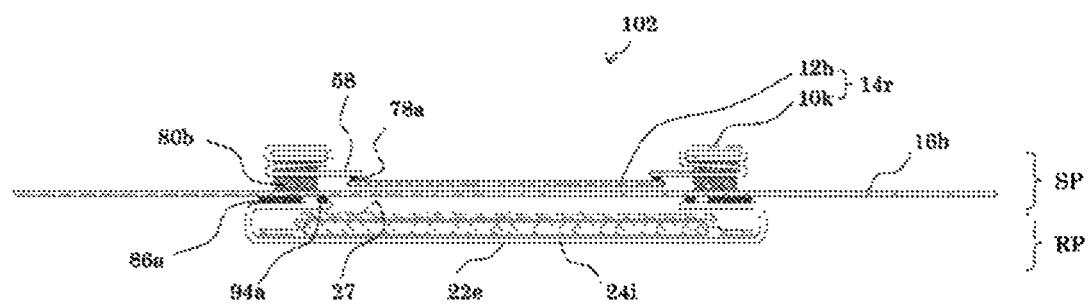
Figure 12C:
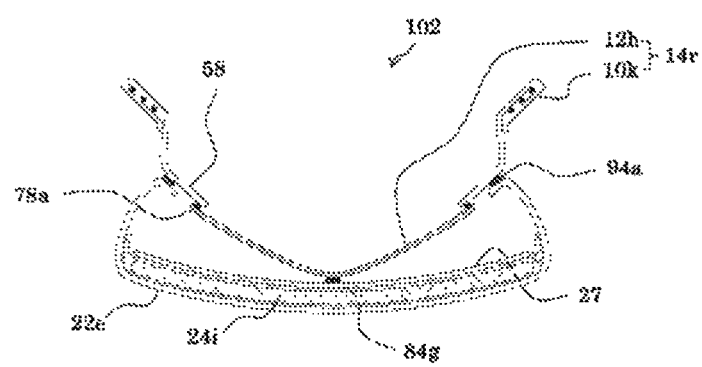

FIG. 12 contains schematic diagrams illustrating a further example of an implementation aspect of an absorbent article according to the present invention. FIG. 12(A) is a plan developed view schematically showing the state in which stress is applied to the absorbent article, in the form of a tape-type diaper, such that it is pulled in the front-rear direction and the lateral direction in order to be developed into a substantially planar form. FIG. 12(B) is a lateral end view along line XIIB-XIIB in FIG. 12(A) in the above-described state. FIG. 12(C) is a lateral end view along line XIIC-XIIC in FIG. 12(A) when stress is not applied to the absorbent article (relaxed state). It should be noted that, in the following description, the materials of the respective members are illustrative.

Absorbent article 102 shown in FIG. 12 is configured as a tape-type diaper for infants (M size (for body weight of approximately 6 to 11 kg)).

The sizes of the respective members of absorbent article 102 described hereinafter are examples in the case of M size and they can be changed as appropriate. It should also be understood that, when the size of the absorbent article is different, the sizes of the respective members will also change. The sizes of the respective members of absorbent article 102 described hereinafter are the sizes in the tension state, unless otherwise stated.

Absorbent article 102 is provided with body-contacting part SP and body-non-contacting part RP. Body-contacting part SP includes: canal member 14r having a pair of right and left head parts 10k extending in the front-rear direction and having stretchability at at least part thereof and canal sheet 12h in which both the right and left edges thereof are coupled to the pair of right and left head parts 10k and the center part thereof hangs downward at the time of wearing; and front covering-part 16b and rear covering-part 18b, which function as fixing members that fix canal member 14r to the wearer's body such that head parts 10k of canal member 14r make contact with the wearer's skin at the time of wearing. Body-non-contacting part RP includes: leak preventer 22c in sheet form that prevents a bodily fluid from leaking; and absorber 24i which is arranged on the upper side of leak preventer 22e and which is capable of absorbing the bodily fluid.

S-part SP has a total length of 450 mm and a total width of 340 mm.

The canal sheet member has a total length of 370 mm and a total width of 120 mm. Pair of right and left head parts 10k has a width of 15 mm.

Front covering-part 16b has a total length of 70 mm. Rear covering-part 18b has a total length of 90 mm.

R-part RP has a total length of 370 mm and a total width of 140 mm.

Absorber 24i is rectangular and has a total length of 340 mm and a total width of 110 mm.

The under surfaces of the leading end parts of inner extension parts 58 (having a length of 40 mm in the lateral direction), where no polyurethane filament of the pair of right and left head parts 10k is present, and canal sheet 12h are coupled together at coupling parts 78a.

The S-part is of a separate body coupling type shown in FIG. 6(A).

The under surfaces of the front and rear end pairs of canal member 14r (more specifically, the under surfaces of parts of the pair of right and left head parts 10k, which are closer to the outside than coupling parts 78a of inner extension parts 58) and the upper surfaces of front covering-part 16 and rear covering-part 18 are respectively coupled together, in a continuous manner in belt form, at canal part-front end coupling part 80*b* and canal part-rear end coupling part 82*b*, by means of a hot-melt adhesive, and are therefore integrated together such that a leak prevention property is obtained.

Canal member 14*r* includes a pair of right and left head parts 10*k* (which are configured by coupling, in an extended stale, the upper surfaces and under surfaces of three polyurethane filaments to a non-woven fabric that serves as a support by means of an adhesive) and liquid permeable canal sheet 12*h* (which is a PE/PP spunbonded non-woven fabric being applied with hydrophilization process and having a basis weight of 15 g/m$^2$) which connects between the pair of right and left head parts 10*k*. Fine pores provided in liquid permeable canal sheet 12*h* function as passages for transferring a bodily fluid from the upper side of canal sheet 12*h* onto the surface of absorber 24*i*.

Each of front covering-part 16*b* and rear covering-part 18*b* is configured by one non-woven fabric (which is a PP SMMS non-woven fabric having a basis weight of 15 g/m$^2$).

Detachable members 30*b* (Velcro tape (male)) are provided on both the right and left sides of rear covering-part 18*b*. Detachable members (not shown) are also provided on the under surface of front covering-part 16*b*, such that they can be detached from detachable members 30*b*. In this manner, absorbent article 102 constitutes a tape-type diaper.

The front end of canal member 14*r* is arranged such that it is located at the position 30 mm posterior to the front end of front covering-part 16*b*. The front end and the right and left side edges around such front end of canal member 14*r* and the under surface of front covering-part 16*b* are coupled together by means of a hot-melt adhesive. The rear end of canal member 14*r* is arranged such that it is located at the position 50 mm anterior to the rear end of rear covering-part 18*b*. The rear end and the right and left side edges around such rear end of canal member 14*r* and the under surface of rear covering-part 18*b* are coupled together by means of a hot-melt adhesive.

In the R-part, absorber 24*i* is arranged on the upper side of leak preventer 22*e* in sheet form and its upper surface is covered by liquid permeable core wrapping sheet 27. Leak preventer 22*e* and core wrapping sheet 27 are coupled together on both the right and left edges by means of a hot-melt adhesive so as to prevent absorber 24*i* from leaking out.

Leak preventer 22*c* is a laminated body made up of a PE air permeable film having a thickness of 18 μm and a PP/PE spunbonded non-woven fabric having a basis weight of 12 g/m$^2$.

Absorber 24*i* is an absorber in which a mixture of SAP and pulp (SAP/pulp=60/40 (mass ratio)) is compressed to a thickness of 1.5 mm and which is covered by a tissue having a basis weight of 20 g/m$^2$.

Core wrapping sheet 27 is a PP spunbonded non-woven fabric which is applied with surface hydrophilization process and which has a basis weight of 13 g/m$^2$.

Between the S-part and the R-part, part of the under surface of canal sheet 12*h* (i.e. the underside surface of the bottom surface of the canal part configured by canal sheet 12*h*) and part of the surface of absorber 24*i* (or the surface of core wrapping sheet 27) are coupled together at linear bottom surface coupling part 84*g* (having a length of 120 mm and a width of 5 mm), which extends from crotch part C to and over front body F, by means of a hot-melt adhesive.

In addition, the under surfaces of front covering-part 16*b* and rear covering-part 18*b* of the S-part and the right and left edge parts folded back to the upper side of leak preventer 22*e* (being parts where absorber 24*i* and core wrapping sheet 27 are not present) are respectively coupled together at R-part-front end coupling part 86*a* and R-part-rear end coupling part 88*a*.

Furthermore, the under surfaces of inner extension parts 58 of the pair of right and left head parts 10*k* of the S-part and the right and left edge parts folded back to the upper side of leak preventer 22*e* (which are parts where absorber 24*i* and core wrapping sheet 27 are not present) are coupled together at S-part-R-part side edge coupling parts 94*a* at crotch part C.

In this way, the S-part and the R-part are integrated together. The front coupling and the rear coupling, as well as the right and left edge part coupling, between the S-part and the R-part play a role of reinforcing the coupling at bottom surface coupling part 84*g*.

As shown in FIG. 12(C), in the relaxed state, the interval between the pair of right and left head parts 10*k* of canal member 14*r* of the S-part becomes narrow (approximately 40 mm at crotch part C) and the canal part formed by canal sheet 12*h* is deepened (deepest at crotch part C) and thus, assumes a V-shape or U-shape. At the time of wearing absorbent article 102, only the pair of right and left head parts 10*k* having stretchability at at least part thereof make contact with the wearer's skin, and it is thereby ensured that the R-part including absorber 24*i* is spaced apart from the wearer's skin.

When a wearer excretes a bodily fluid, the excreted bodily fluid is received on the upper side of canal sheet 12*h*. Thereafter, it transfers from the upper side of canal sheet 12*h* onto the surface of absorber 24*i* through the above-described passage while it shifts in the front-rear direction.

Figure 13A:
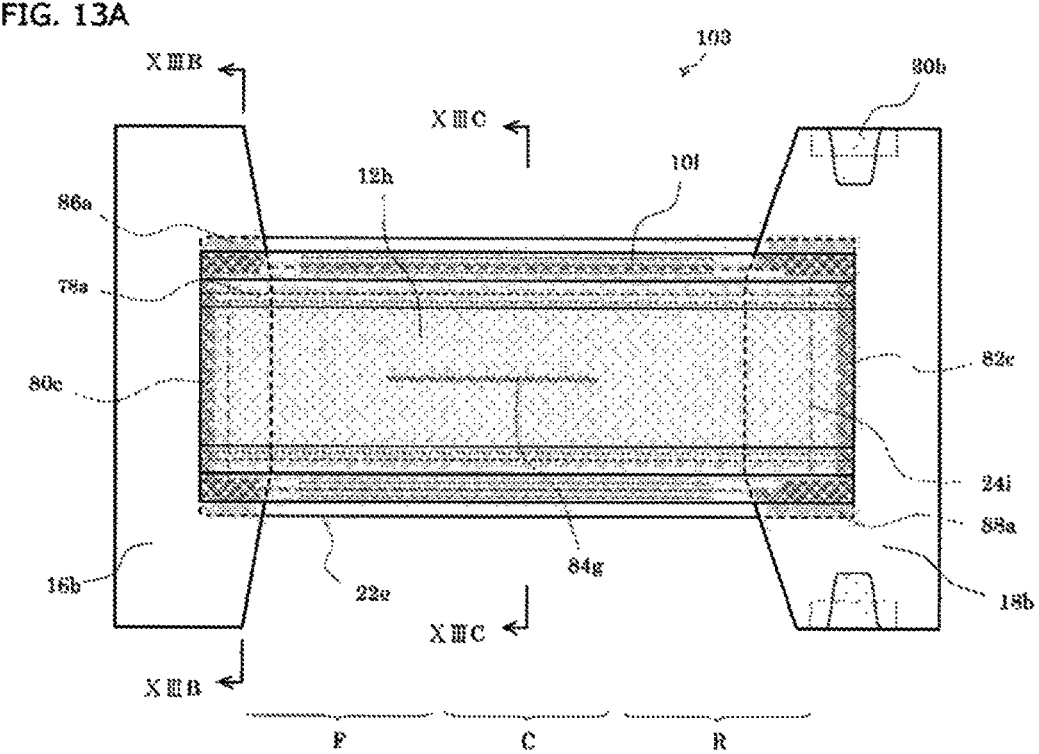
Figure 13B:
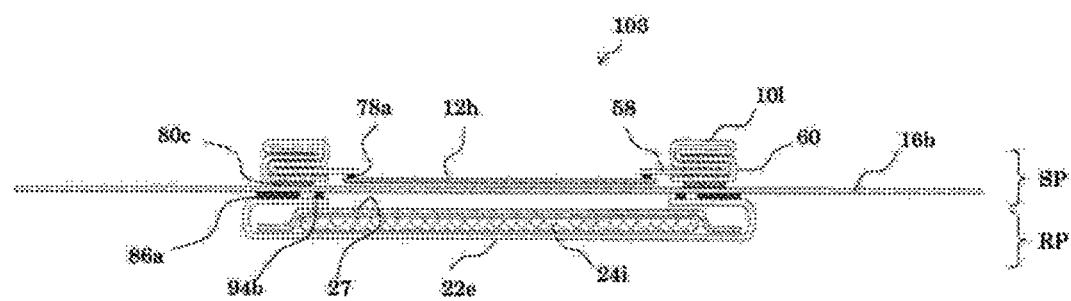
Figure 13C:
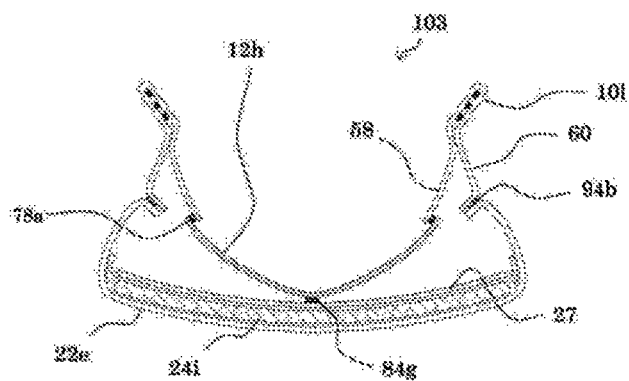

FIG. 13 contains schematic diagrams illustrating a further example of an implementation aspect of an absorbent article according to the present invention. FIG. 13(A) is a plan developed view schematically showing the state in which stress is applied to the absorbent article, in the form of a tape-type diaper, such that it is pulled in the front-rear direction and the lateral direction in order to be developed into a substantially planar form. FIG. 13(B) is a lateral end view along line XIIIB-XIIIB in FIG. 13(A) in the above-described state. FIG. 13(C) is a lateral end view along line XIIC-XIIC in FIG. 13(A) when stress is not applied to the absorbent article (relaxed state).

Absorbent article 103 shown in FIG. 13 is similar to absorbent article 102 shown in FIG. 12; however, it differs therefrom with respect to the point that the pair of right and left head parts 10*l* have outer extension parts 60 (having a length of 30 mm in the lateral direction).

Outer extension part 60 is coupled to each of front covering-part 16*b* and rear covering-part 18*b* at canal part-front end coupling part 80*c* and canal part-rear end coupling part 82*c*.

Absorbent article 103 differs from absorbent article 102 with respect to the point that outer extension parts 60 are coupled to leak preventer 22*e* at S-part-R-part side edge coupling parts 94*b*.

As compared to absorbent article 102 of the present invention shown in FIG. 12, absorbent article 103 shown in FIG. 13 has a higher degree of freedom in terms of the movement of the pair of right and left head parts 10*l* in the lateral direction.

Figure 14A:
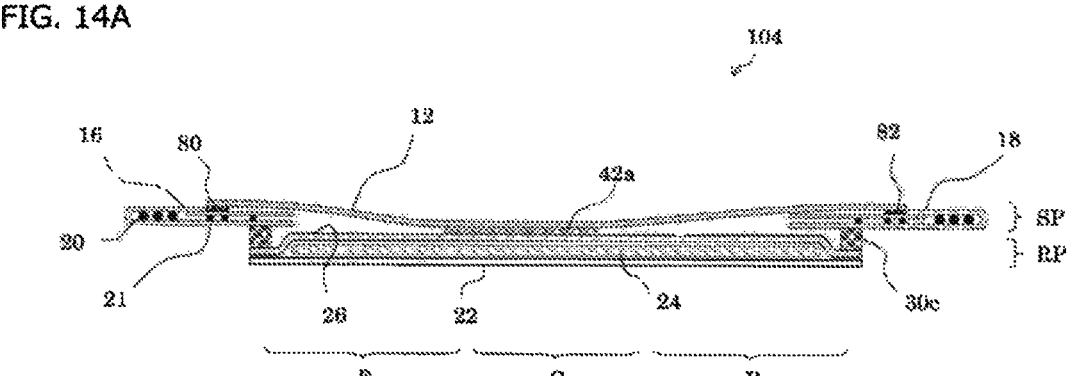
Figure 14B:
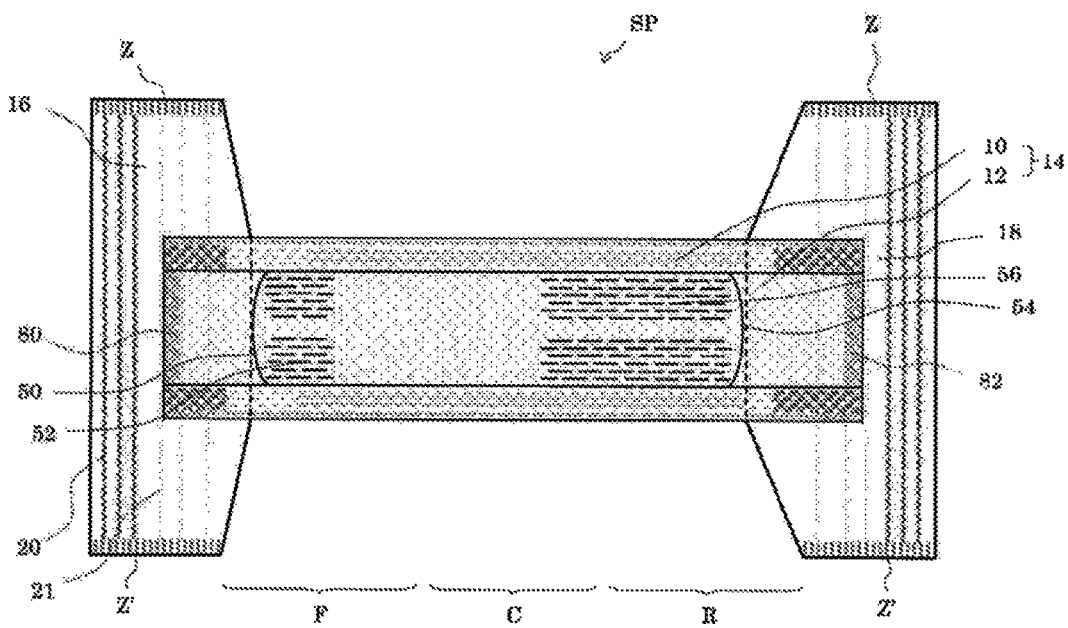
Figure 14C:
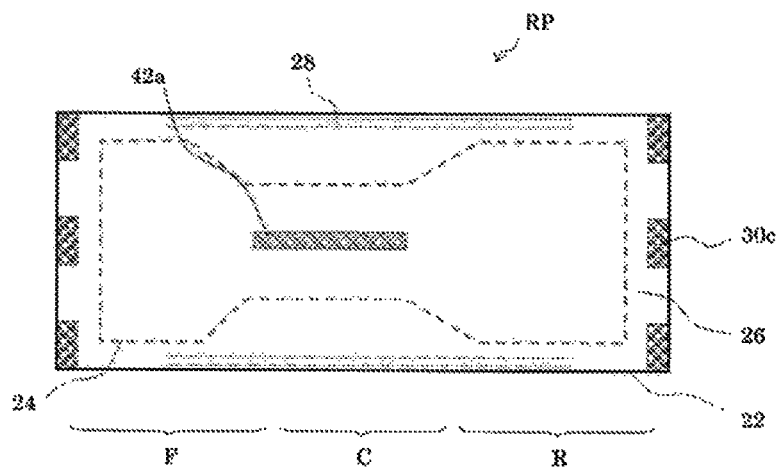

FIG. 14 contains schematic diagrams illustrating a further example of an implementation aspect of an absorbent article according to the present invention. FIG. 14(A) is a longitudinal end view at the center part in the lateral direction in the state in which the absorbent article, in the form of a pants-type diaper, is cut at abdominal sealing parts (Z and Z' in FIG. 14(A)) on both the right and left sides of the waist gather thereof, and in which stress is applied to the absorbent article such that it is pulled in the front-rear direction and the lateral direction in order to be developed into a substantially planar form. FIG. 14(B) is a plan view of the S-part in the above-described state. FIG. 14(C) is a plan view of the R-part in the above-described state.

Absorbent article 104 shown in FIG. 14 is similar to absorbent article 101 of the present invention shown in FIG. 11; however, it differs therefrom with respect to the point that the S-part and R-part are detachable and to the point of the sizes of the respective members. It should be noted that, in the description hereinafter, the materials for the respective members are illustrative.

Absorbent article 104 shown in FIG. 14 is configured as a pants-type diaper for infants (Super Big size (for body weight of approximately 13 to 25 kg)).

The sizes of the respective members of absorbent article 104 described hereinafter are examples in the case of Super Big size and they can be changed as appropriate. It should also be understood that, when the size of the absorbent article is different, the sizes of the respective members will also change. The sizes of the respective members of absorbent article 104 described hereinafter are the sizes in the tension state, unless otherwise stated.

S-part SP has a total length of 690 mm and a total width of 360 mm (200 mm in the relaxed state).

The canal sheet member has a total length of 750 mm and a total width of 140 mm. Canal sheet 12 has a width of 220 mm when the folded-back parts are unfolded. Each head part in the pair of right and left head parts 10 has a width of 20 mm.

Front covering-part 16 has a total length of 130 mm. Rear covering-part 18 has a total length of 160 mm.

R-part RP has a total length of 500 mm and a total width of 210 mm.

Absorber 24 has an hourglass shape in which the width is narrowed in crotch part C, and has a total length of 430 mm and a total width of 170 mm, at the maximum, and 90 mm, at the minimum.

The configuration by which the S-part and the S-part are allowed to be detachable will now be described.

Detachable members 30c (Velcro tape (male)) are provided at three locations in the lateral direction at each of the front end and the rear end of surface sheet 26 of the R-part.

Although not shown, detachable members (TLZs (female)), which are detachable from detachable members 30c, are provided on the under surface of each of front covering-part 16 and rear covering-part 18 of the R-part.

The positions at which detachable members 30c of the R-part couple in a detachable manner are the position approximately 35 mm posterior to the front end of front covering-part 16 of the S-part and the position approximately 35 mm anterior to the rear end of rear covering-part 18.

In addition, adhesive member 42a (having a length in the front-rear direction of 120 mm and a width in the lateral direction of 5 mm) that extends in the front-rear direction is provided, at crotch part C, in the center part in the lateral direction of surface sheet 26 that covers absorber 24 of the R-part, and thus, surface sheet 26 is made detachable from the under surface (i.e. bottom surface part of the canal part) of canal sheet 12 of the S-part.

In this way, based on the action of detachable members 30c, the detachable members that are detachable from detachable members 30c and adhesive member 42a, the S-part and the R-part are made detachable.

As described above, the absorbent article according to the present invention is illustrated based on the respective embodiments illustrated herein; however, it should be noted that the present invention is not limited to these embodiments and, for example, the configurations of the respective parts may be replaced with any configuration capable of performing a similar function.

In addition, the configurations of the respective parts in the respective embodiments may be combined in an arbitrary manner to obtain other embodiments.

The absorbent article according to the present invention may be preferably used for paper diapers (for infants and adults), incontinence articles, training pants, female sanitary napkins or the like.

DESCRIPTIONS OF REFERENCE NUMERALS

| | |
|---|---|
| 10, 10a, 10b, 10c, 10d, 10e, 10f, 10g, 10h, 10i, 10j, 10k, 10l | head part |
| 11 | elastic yarn |
| 11a, 11b, 11d | foam member |
| 11c | rubber sheet member |
| 12, 12a, 12b, 12c, 12d, 12e, 12f, 12g, 12h | canal sheet |
| 14, 14a, 14b, 14c, 14d, 14e, 14f, 14g, 14h, 14i, 14j, 14k, 14l, 14m, 14n, 14o, 14p, 14q, 14r | canal member |
| 15 | liquid impermeable film |
| 15a, 15b | liquid impermeable foam member |
| 15c | liquid-absorbing foam member |
| 15d | hydrophilic bulky web |
| 16, 16a, 16b | front covering-part |
| 18, 18a, 18b | rear covering-part |
| 20 | waist gather |
| 21 | shirring gather |
| 22, 22a, 22b, 22c, 22d, 22e | leak preventer |
| 26, 26a, 26b, 26c | surface sheet |
| 27 | core wrapping sheet |
| 28, 28a, 28b | stretchable member |
| 30, 30a, 30b, 30c | detachable member |
| 32 | canal bottom surface part |
| 34 | canal left side surface part |
| 36 | canal right side surface part |
| 38 | left side covering part |
| 40 | right side covering part |
| 42, 42a | adhesive member |
| 44 | front, pocket part |
| 46 | rear pocket part |
| 48 | diffusion sheet |
| 50 | front part slit |
| 52 | group of front part slit |
| 54 | rear part slit |
| 52 | group of rear part slit |
| 58 | inner extension part |
| 60 | outer extension part |
| 78, 78a, 90 | coupling part |
| 80, 80a, 80b, 80c | canal part-front end coupling part |
| 82, 82a, 82b, 82c | canal part-rear end coupling part |
| 84, 84a, 84b, 84c, 84d, 84e, 84f, 84g | bottom surface coupling part |
| 86, 86a | R-part-front end coupling part |
| 88, 88a | R-part-rear end coupling part |
| 92, 92a | Side surface coupling part |
| 94, 94a, 94b | S-part-R-part side edge coupling part |
| 100, 100a, 100b, 100c, 100d, 100e, 100f, 101, 102, 103, 104 | absorbent article |
| C | crotch part |
| F | front body |
| R | rear body |
| RP | body-non-contacting part |
| SP | body-contacting part |
| Z, Z' | abdominal sealing part |

The invention claimed is:

1. An absorbent article for a wearer to wear, comprising:
a body-contacting part configured to contact the wearer's body at the time of wearing, including
a canal member that has
a pair of right and left head parts extending in the front-rear direction and having stretchability at at least part thereof, and
a canal sheet in which right and left edges thereof couple to the pair of right and left head parts, respectively, and in which a center part thereof hangs downward at the time of wearing, the canal sheet having an upper side configured to make contact with the wearer's skin at the time of wearing and to receive bodily fluid excreted by the wearer, and
a pair of covering parts configured to fix the canal member to the wearer's body in order to allow the head parts of the canal member to make contact with the wearer's skin at the time of wearing,
a body-non-contacting part including
a leak preventer in sheet form that prevents leakage of the bodily fluid, and
an absorber arranged on an upper side of the leak preventer and capable of absorbing the bodily fluid,
wherein the body-non-contacting part includes, in the front-rear direction, a front part, a rear part, and a crotch part between the front part and the rear part, each of right edge and left edge of the body-non-contacting part not being attached to any portion of the body-contacting part in the crotch part, and each of right edge and left edge of the body-contacting part not being attached to any portion of the body-non-contacting part in the crotch part,
wherein the body-non-contacting part does not contact the wearer's body at the time of wearing,
wherein a passage is provided for transferring the bodily fluid from the upper side of the canal sheet onto a surface of the absorber,
a part of an under surface of the canal sheet and a part of the surface of the absorber are coupled together,
the absorber is spaced apart by the canal sheet from the wearer's skin at the time of wearing, and
when the wearer excretes the bodily fluid, the excreted bodily fluid is received on the upper side of the canal sheet, and thereafter the bodily fluid is transferred from the upper side of the canal sheet onto the surface of the absorber through the passage while shifting in the front-and-rear direction.

2. The absorbent article according to claim 1, wherein
a part of the center part in the lateral direction of the under surface of the canal sheet and a part of the surface of the absorber are coupled together at a bottom surface coupling part.

3. The absorbent article according to claim 2, wherein the bottom surface coupling part extends in the front-rear direction in an area including the crotch part.

4. The absorbent article according to claim 2, wherein
a part of vicinities of right and left edge parts of the under surface of the canal sheet and a part of the surface of the absorber are coupled together at right and left side surface coupling parts.

5. The absorbent article according to claim 4, wherein the right and left side surface coupling parts extend in the front-rear direction in the area including the crotch part.

6. The absorbent article according to claim 1, wherein the pair of covering parts includes a front covering-part that covers the front body and a rear covering-part that covers the rear body.

7. The absorbent article according to claim 6, including a detachable member that couples the front covering-part and the rear covering-part in a detachable manner.

8. The absorbent article according to claim 6, wherein the front covering-part and the rear covering-part are integrated together and cover around an abdominal part of the wearer at the time of wearing.

9. The absorbent article according to claim 1, wherein at least part of the canal sheet is liquid impermeable.

10. The absorbent article according to claim 1, wherein at least part of the pair of covering parts is liquid impermeable.

11. The absorbent article according to claim 1, wherein right and left edge parts of the leak preventer have stretchable bodies that provide an effect of reducing the length of the right and left edge parts in the front-rear direction.

12. The absorbent article according to claim 1, wherein the leak preventer has a shape which is convex to the lower side at the time of wearing in at least the crotch part.

13. The absorbent article according to claim 1 wherein
a distance between the surface of the absorber and the wearer's skin at the time of wearing becomes 5 mm or more.

14. The absorbent article according to claim 1, wherein the body-contacting part and the body-non-contacting part are detachable.

15. A method of producing an absorbent article according to claim 1, the method comprising:
a step of forming each of the body-contacting part and the body-non-contacting part; and
a step of, thereafter, coupling the body-contacting part and the body-non-contacting part.

16. The absorbent article according to claim 1, wherein the body-non-contacting part includes a surface sheet on an upper side of the absorber to have the absorber sandwiched between the surface sheet and the leak preventer, the surface sheet not being in contact with the wearer's body at the time of wearing.

* * * * *